(12) United States Patent
Wiersma et al.

(10) Patent No.: US 9,782,607 B2
(45) Date of Patent: Oct. 10, 2017

(54) SYSTEMS AND METHODS FOR RADIATION TREATMENT PLANNING USING COMBINED IMAGING AND TREATMENT DOSE

(71) Applicants: Rodney Wiersma, Chicago, IL (US); Zachary Grelewicz, Chicago, IL (US)

(72) Inventors: Rodney Wiersma, Chicago, IL (US); Zachary Grelewicz, Chicago, IL (US)

(73) Assignee: The University of Chicago, Chicago, IL (US)

( * ) Notice: Subject to any disclaimer, the term of this patent is extended or adjusted under 35 U.S.C. 154(b) by 254 days.

(21) Appl. No.: 14/818,808

(22) Filed: Aug. 5, 2015

(65) Prior Publication Data

US 2016/0038767 A1    Feb. 11, 2016

Related U.S. Application Data

(60) Provisional application No. 62/033,533, filed on Aug. 5, 2014.

(51) Int. Cl.
| | | |
|---|---|---|
| *A61N 5/10* | (2006.01) | |
| *A61B 6/00* | (2006.01) | |
| *A61B 6/03* | (2006.01) | |

(52) U.S. Cl.
CPC ............ *A61N 5/1039* (2013.01); *A61B 6/542* (2013.01); *A61N 5/1031* (2013.01); *A61B 6/032* (2013.01); *A61B 6/4085* (2013.01); *A61B 6/487* (2013.01)

(58) Field of Classification Search
CPC .... A61N 5/1031; A61N 5/1039; A61B 6/542; A61B 6/487; A61B 6/032; A61B 6/4085
USPC ........................................ 378/62, 65
See application file for complete search history.

(56) References Cited

U.S. PATENT DOCUMENTS

| | | | | |
|---|---|---|---|---|
| 2008/0267351 A1* | 10/2008 | Spies | ................... | A61N 5/1039 378/65 |
| 2012/0230462 A1* | 9/2012 | Robar | ................... | A61N 5/1049 378/4 |

* cited by examiner

*Primary Examiner* — Courtney Thomas
(74) *Attorney, Agent, or Firm* — Quarles & Brady LLP

(57) ABSTRACT

Systems and methods for radiation treatment planning that integrate the MV therapeutic radiation dose imparted to a subject together with the kV imaging radiation dose imparted to a subject during radiation therapy are provided. For instance, dose optimization is based on the combined effect of both a kV imaging dose that is imparted to the subject during the image guided radiation treatment procedure and the therapeutic dose delivered to the subject by a treatment radiation source, such as an MV source. Using this optimization, the kV beam and MV beam are equally treated as radiation producing sources and are thus optimized together at the treatment planning stage to produce a patient treatment plan that optimally uses the kV imaging dose. Thus, the kV beam is treated both as an additional source of therapeutic radiation and as a tool for imaging the subject.

19 Claims, 13 Drawing Sheets

SYSTEMS AND METHODS FOR RADIATION TREATMENT PLANNING USING COMBINED IMAGING AND TREATMENT DOSE

CROSS-REFERENCE TO RELATED APPLICATIONS

This application claims the benefit of U.S. Provisional Patent Application Ser. No. 62/033,533, filed on Aug. 5, 2014, and entitled "SYSTEMS AND METHODS FOR RADIATION TREATMENT PLANNING USING COMBINED IMAGING AND TREATMENT DOSE."

BACKGROUND OF THE INVENTION

The field of the invention is systems and methods for radiation treatment planning. More particularly, the invention relates to systems and methods for producing a treatment plan for an image-guided radiation treatment system that accounts for utilizing the imaging dose as part of the treatment dose.

Numerous studies over the years have demonstrated the feasibility of both marker and markerless based kiloVolt ("kV") fluoroscopic tracking. Compared to external patient surface monitoring, using either IR markers or 3D surface imaging, kV tracking has the benefit of direct tumor position monitoring, and therefore avoids potential issues with poor external-to-internal tumor correlation.

Another advantage of kV imaging is its ability to resolve lower contrast anatomical information than megavolt ("MV") electronic portal imaging devices ("EPID"), which typically rely on the use of surgically implanted fiducial markers for target location. The use of such markerless kV tracking is especially attractive for the lung, where percutaneous implantation of fiducial markers is an invasive and costly surgical procedure that carries the risk of pneumothorax. Although a combined MRI-LINAC approach is one potential modality for performing markerless real-time lung tumor motion tracking, such systems are still in the early developmental stage, and are likely to be extremely complex and expensive. Because most modern LINACs are now pre-equipped with on-board kV imaging sources, performing real-time lung tumor tracking through the use of kV imaging is a potential cost effective solution.

Clinical adoption of real-time kV based tracking has been held back by concern over the excess kV imaging dose cost to the patient when imaging in continuous fluoroscopic mode. This includes tracking with two or more kV imagers mounted either to the ceiling or the floor of the treatment room, or two kV imagers mounted to the gantry, or a single kV imager mounted on the LINAC gantry.

Because the problem of high imaging dose associated with real time kV fluoroscopic tumor tracking has long been acknowledged, there are a number of recent studies investigating techniques to reduce the kV imaging dose. Many of these studies use additional information to limit the frequency of kV imaging. In one such study, stereoscopic MV-kV imaging of a fiducial marker is performed at the start of therapy in order to build a correlation model, so that, subsequently, kV imaging is only required intermittently when the fiducial is not visible in the MV image.

Another study, reported on the Cyberknife Synchrony system. In this system, an internal/external correlation model was first developed in order to track the tumor motion via externally visible marker tracking. However, the model was updated throughout the course of treatment via the acquisition of new x-ray images once every 1-5 minutes. The study reported that the synchrony system reduced the 3D positional error, though some error was still present. Other studies have investigated coupling fluoroscopy with external surface cameras, rather than external marker cameras.

The dosimetric effect of real-time motion tracking with kV imaging and fiducial markers have been investigated, with numbers often in the range of 1 cGy per minute at the surface for relatively low mAs. Depending on the imaging requirements, the fluence rate may escalate, suggesting that for real-time kV planar imaging to be incorporated safely into image-guided radiation therapy IGRT procedures, the dosimetric effects should be carefully considered prior to treatment. This is especially a concern for markerless tracking, where low contrast tissues and large anatomical features may require the use of higher kV fluences and larger kV aperture sizes than with metallic fiducial markers. Due to the variety of patient anatomical sizes, and the complexity of the kV beam arrangements typically needed for real-time tracking, it is necessary to perform a patient specific kV dose calculation in order to fully understand the exact impact of the kV imager.

Volumetric measurements, such as cone beam CT ("CBCT"), have been shown to improve the accuracy of patient setup for lung stereotactic body radiotherapy ("SBRT"), conventional radiotherapy, and IMRT (Bissonnette, et al., 2009) (Den, et al, 2010). As a result, daily CBCT is increasingly included as a part of patient treatment protocols. Daily in-room CBCT can take one of two forms: Megavoltage (MV) CBCT (Pouliot, et al., 2004), or kilovoltage (kV) CBCT (Schreibmann, et al., 2005). Measurements of radiation dose for either technique have been previously studied (Hyer, et al., 2010) (Islam, et al., 2006) (Gayou, et al., 2007), and at this point, incorporation of MV CBCT dose into the treatment plan has been reported on (Miften, et al., 2007).

There have been early investigations into the incorporation of kV CBCT dose into the treatment plan (Alaei, et al., 2009) (Dzierma, et al., 2013). In one such study, in an anthropomorphic phantom, thoracic CBCT was found to result in doses in the range of 6.04-8.98 mGy in the lungs and 3.93-6.23 mGy in the spinal cord, among reported dose values at other typical organ at risk (OAR) sites. These values will tend to be specific to both patient geometry and imaging protocol.

CBCT and fluoroscopy share the similarity that one of the primary concerns of either imaging procedure is excessive skin dose. Therefore a method of incorporating kV CBCT dose into the patient treatment plan at the point of treatment planning, and assessing the effect of the kV CBCT dose on the overall treatment plan quality and on skin dose reduction is needed.

SUMMARY OF THE INVENTION

The present invention addresses the aforementioned drawbacks by providing a method for producing an IGRT treatment plan that includes an imaging radiation source that emits an imaging radiation beam and a treatment radiation source that emits a treatment radiation beam.

As is typical with a treatment planning system (TPS), 3D patient data obtained from a CT is transferred to the TPS and 3D targets are contoured to define gross tumor volume (GTV), clinical target volume (CTV), organs at risk (OAR), and other relevant anatomical structures. The physician then prescribes a treatment dose to the CTV, assigns dose limits to the OARs, and indicates kV imaging preferences (kV fluoro, daily CBCT, daily CT-on-rails, 4DCT, etc). Using the 3D patient information, along with physician prescribed dose constraints and imaging preferences, the invention creates a unique objective function that includes both prescribed dose constraints together with kV imaging beam constraints. The objective function is then optimized using inverse optimization techniques to determine the best MV treatment beams and kV imaging beams configurations.

In certain embodiments, a first dose attributable to the imaging radiation source beam is calculated based on the provided model of the imaging radiation beam, and a second dose attributable to the treatment radiation source beam is calculated based on the provided model of the treatment radiation beam.

In alternative embodiments, the dose is calculated at every iteration of the optimization algorithm. The treatment planning system is then directed to produce a radiation treatment plan by optimizing an objective function based on the first and second doses, subject to a constraint that accounts for beam-on time for both the imaging radiation beam and the treatment radiation beam.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

BRIEF DESCRIPTION OF THE DRAWINGS

FIG. 3A illustrates MV dose from MV+kV optimization. FIG. 3B illustrates MV dose from standard IMRT (no imaging). FIG. 3C illustrates kV dose from MV+kV optimization. FIG. 3D illustrates kV dose from standard, non-optimized fluoroscopic tracking. In each case, the PTV is indicated by a black outline.

FIG. 4A illustrates MV dose from MV+kV optimization. FIG. 4B illustrates MV dose from standard IMRT (no imaging). FIG. 4C illustrates kV dose from MV+kV optimization. FIG. 4D illustrates kV dose from standard, non-optimized fluoroscopic tracking. In each case, the PTV is indicated by a black outline.

FIG. 5A illustrates MV dose from MV+kV optimization. (b) MV dose from standard IMRT (no imaging). (c) kV dose from MV+kV optimization. (d) kV dose from standard, non-optimized fluoroscopic tracking. In each case, the PTV is indicated by a black outline.

FIG. 6A illustrates MV dose from MV+kV optimization. FIG. 6B illustrates MV dose from standard IMRT (no imaging). FIG. 6C illustrates kV dose from MV+kV optimization. FIG. 6D illustrates kV dose from standard, non-optimized fluoroscopic tracking. In each case, the PTV is indicated by a black outline.

FIG. 14A illustrates an aperture defined by a 3×3 beamlet selection centered in a 5×5 array.

FIG. 14B illustrates an aperture defined by moving leafs in a multi-leaf collimator to add one beamlet to the aperture of FIG. 14A and to remove one beamlet from the aperture of FIG. 14A.

FIG. 16A shows DVH curves for MV optimization with no imaging. FIG. 16B shows DVH curves for MV optimization without optimized imaging. FIG. 16C shows DVH curves for MV+kV optimization.

DETAILED DESCRIPTION OF THE INVENTION

Described here are systems and methods for radiation treatment planning that integrate the radiation dose imparted to a subject by an imaging radiation source during an image-guided radiation treatment. For instance, a kilovolt ("kV") imaging dose that is imparted to the subject during the image guidance of the radiation treatment is accounted for and treated as a part of the therapeutic dose otherwise delivered to the subject by a treatment radiation source, such as a megavolt ("MV") source. Thus, the kV beam is treated both as an additional source of therapeutic radiation and as a tool for imaging and dynamically tracking the tumor. As described below, in some instances the kV beam can be from a fluoroscopic imaging system and in some other instances the kV beam can be from a cone beam computed tomography ("CBCT") imaging system. In general, however, the kV beam from any suitable x-ray imaging system can be accounted for as an additional source of therapeutic radiation. In some instances, magnetic resonance imaging ("MRI") images can also be used for treatment planning.

The present invention is therefore capable of informing a radiation treatment plan about the contribution of kV dose to the planning target volume ("PTV"), skin, and other organs-at-risk ("OARs"); how the kV imaging dose affects the overall optimization of the MV beam fluences; and whether the chosen mAs and frame rate values lead to an imaging dose that is too high to be safely applied.

The present invention represents a departure from the existing image guided radiation therapy ("IGRT") treatment planning paradigm where kV imaging dose is considered as unwanted and in excess of the planned MV treatment dose.

The method of incorporating the kV dose and imaging constraints into the treatment planning algorithm is general to intensity modulated radiation therapy ("IMRT"), and is not aimed to any particular treatment site or imaging modality; however, for the examples described herein, the patient data used for simulation would most closely represent the situation of gated IMRT with real-time kV tumor tracking for lung cancer patients. In most cases, lung cancer is treated with three-dimensional conformal radiation therapy ("3DCRT") because of the challenges of applying IMRT in the presence of large respiratory motion. Gated lung IMRT, however, can offer higher target conformality than 3DCRT, thereby allowing potential dose escalation and more healthy tissue sparing.

Figure 1:
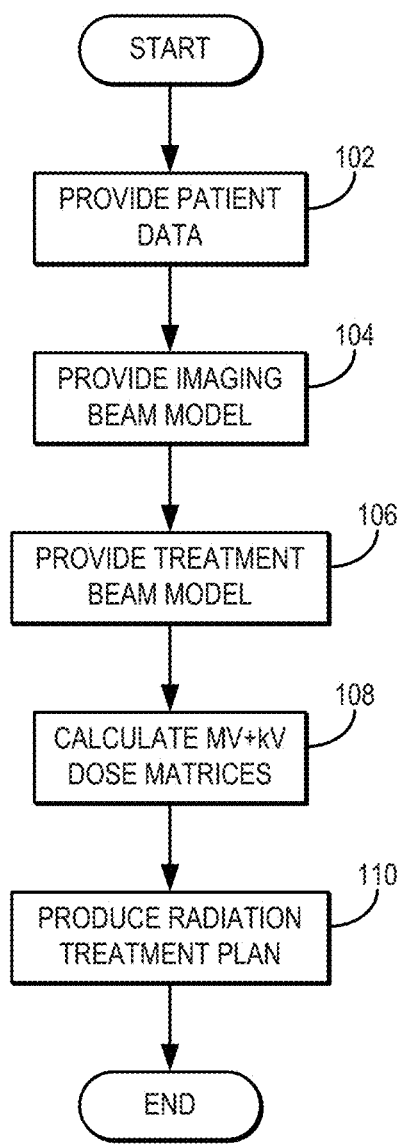
FIG. 1 is a flowchart setting forth the steps of an example method for producing a radiation treatment plan that accounts for both an imaging beam dose and a treatment beam dose.

Referring now to FIG. 1, a flowchart setting forth the steps of an example method for producing a radiation treatment plan for an image-guided radiation treatment system that incorporates dose attributed to both an imaging source and a treatment source is illustrated. In some embodiments, the image-guided radiation treatment system can be an IMRT system. In some other embodiments, the image-guided radiation treatment system can be a volumetric modulated arc therapy system.

The method begins by providing patient data associated with the patient that will be receiving radiation treatment, as indicated at step 102. For instance, the patient data may include medical images of the patient, such as previously acquired medical images that depict the patient's anatomy. As an example, the patient data may include images acquired with a magnetic resonance imaging ("MRI") system, or with an x-ray computed tomography ("CT") system.

Model data for the radiation beams produced by the imaging source and the therapy source are also provided, as indicated at steps 104 and 106, respectively. As an example, the model data may include phase space files generated for an imaging radiation beam, such as a kV beam, and a therapy radiation beam, such as an MV beam. For example, phase space files can be generated using BEAMnrc or other suitable software. In some embodiments, the model data can be provided by retrieving the model data from a storage device or memory external to the treatment planning system. In some other embodiments, the model data can be provided by retrieving the model data from a storage device or memory internal to the treatment planning system. In still other embodiments, the model data can be provided by computing or otherwise generating the model data using the treatment planning system.

In one specific, non-limiting example, beam modeling can be performed within the EGSnrc Monte Carlo ("MC") environment (Rogers, et al., 1995) for the appropriate treatment system. As one non-limiting example, the MV treatment beam can be modeled in BEAMnrc from the schematics of the Varian Trilogy (Varian Medical Systems, Palo Alto, Calif.) LINAC with flattening filter and 6 MV peak energy. Ideal fluence maps in this example can be modeled with secondary collimators arranged to create bixels with $5\times5$ mm$^2$ openings (defined at SAD=100 cm) in a grid arrangement. Each bixel's phase space file can then be generated from a number of histories, such as 500M histories. Separate MC simulations can be performed to create kV phase space files for different apertures as isocenter, such as $5\times5$, $10\times10$, $15\times15$, $20\times20$, and $20\times27$ cm$^2$ apertures at isocenter, according to the schematics of the Varian Trilogy on-board-imager ("OBI") without half bowtie filter at nominal 125 kVp energy. Different imaging energies, different beam apertures, and different types of filtration may be appropriate for different imaging modalities (e.g., fluoroscopy, CBCT, 4DCT, CT-on-rails).

Based on the patient data and the provided beam model data, influence matrices, or dose matrices, can be computed, as indicated at step 108. As an example, DOSXYZnrc, or other suitable software, can be used to compute the influence matrices.

In one specific, non-limiting example, CT scans of three previously treated lung cancer patients were imported into DOSXYZnrc. Five to ten gantry angles were chosen for each patient, matching the gantry angles from the previously implemented treatment plans. For each gantry angle, dose calculations were performed for the set of MV bixels, and for each of the 125 kV phase space files produced for both patients. The MV dose calculations used 3M histories each, and the kV dose calculations used 16M histories each. Dose calculations were performed on a combination of a distributed computing cluster, and a PC with an Intel Core i7-2600 CPU, with 16 GB RAM.

DOSXYZnrc outputs dose matrices normalized to the number of electrons used to for the original phase space file.

In order to denormalize the dose matrices, the TG-51 (Almond, et al., 1999) machine calibration of 0.85 cGy/MU at 10 cm depth in water for the MV beam was used, with a 400 MU/min dose rate. For kV units, an imaging rate of 7.5 fps, with 80 mA and 32 ms per frame was assumed. The frame rate assumed is likely sufficient for real-time tracking, and the 2.56 mAs per frame is in line with the imaging requirements reported elsewhere. In terms of duty cycle, it is assumed that the kV beam is on only when the MV beam is on. Depending on the imaging need, it may be required to image during the entire course of the treatment, and only deliver MV radiation periodically, as with gated delivery.

Here it is important to note that the kV parameters can be custom adjusted and incorporated in the MV+kV optimization engine according to the user's specific needs. For example, if the kV dose is too high, cutting the frame rate from 7.5 fps to 3 fps will result in substantially lower kV doses. In order to assess the effect of different kV dose rate (in terms of mAs, framerate, and duty cycle), all optimizations were repeated with 20 different weighting factors, $\alpha$, for the kV dose rate.

It will be apparent to one of skill in the art that the optimizing step can be performed using, for example, gradient descent methods, MATLAB (Mathworks, Natick, Mass.) optimization routines, interior point methods, primal-dual methods, simulated annealing, or other stochastic methods.

Based on the calculated dose matrices, a radiation treatment plan is produced, as indicated at step 110. Because the radiation treatment plan is based on both the kV and MV dose matrices, the radiation treatment plan will account for the contribution of the imaging beam dose to the PTV, skin, and other OARs, and will also account for how the imaging beam dose affects the overall optimization of the treatment beam fluences. After the radiation treatment plan is produced, it can optionally be displayed on a graphical user interface. For instance, displaying the radiation treatment plan may include displaying the dose from the imaging radiation beam, displaying the dose from the treatment radiation beam, or displaying a dose from the combination of both the imaging radiation beam and the treatment radiation beam.

In general, the optimization used to produce the radiation treatment plan accounts for both the imaging beam dose and the treatment beam dose by utilizing a modified dose matrix, D, $$D = \begin{bmatrix} d_{11} & \cdots & d_{1M} \\ \vdots & & \vdots \\ d_{N1} & \cdots & d_{NM} \\ d_{(N+1)1} & \cdots & d_{(N+1)M} \\ \vdots & & \vdots \\ d_{(N+L)1} & \cdots & d_{(N+L)M} \end{bmatrix} = \begin{bmatrix} D_{MV} \\ D_{kV} \end{bmatrix}; \quad (1)$$

where the modified dose matrix is a concatenation of the treatment beam dose matrix, $D_{MV}$, and the imaging beam dose matrix, $D_{kV}$.

In IMRT, the dose optimization problem may be formalized as solving the quadratic problem, $$\min_{x \in \mathbb{R}^n} |Dx - p|^2; \quad (2)$$

subject to the linear constraints $x \geq 0$ and $Hx - q > 0$, and where x is an array of n beam weights; D is the $(N+L) \times M$ modified influence matrix, where each element, $d_{ij}$, indicates how much dose the $i^{th}$ beamlet delivers to the $j^{th}$ voxel in a volume containing M voxels; p is the prescription dose to the treatment volume ("PTV"); and $\| \ldots \|_2$ is the L2-norm operation.

The first constraint, $x \geq 0$, ensures that all beamlets are restricted to non-negative values. The second constraint, $Hx - q > 0$, encompasses all upper/lower bound dose constraints and imaging constraints, such that H may be written as, $$H = \begin{bmatrix} H_{DOSE} \\ H_{IM} \end{bmatrix}. \quad (3)$$

Each row of $H_{DOSE}$ corresponds to a voxel in the patient, and the dot product of a row of $H_{DOSE}$ with the beam weight vector, x, gives the total dose to the voxel. The voxels used in $H_{DOSE}$ come from both the PTV and the organs at risk ("OARs").

The submatrix, $H_{IM}$, is a novel way of introducing a hard imaging constraint. It is a constraint on the beam-on time for various bixels, without regard to the dose deposited. This is in contrast to the submatrix $H_{DOSE}$, which is a constraint on the dose deposited to various voxels, without regard to the beam-on time for various bixels. In our case, there are between 64 and 144 MV beamlets for each gantry angle, depending on the size required to encompass the PTV, and a total of 5 (or 10) kV beams. Each row of $H_{IM}$ specifies that the beam-on time for the kV beam orthogonal to a given MV beamlet is at least as long as the beam on time for that beamlet. This model assumes that the total beam on time for a given gantry angle is approximately equal to the total beam on time for the most intense beamlet for that gantry angle. For example, the first row of $H_{IM}$ has the form, $$HM_{IM,1} = [1 \ldots \alpha 0\ 0\ 0\ 0\ 0\ 0] \quad (4);$$

in which the elided portion is filled with zeros, and $\alpha$ is a weighting factor balancing the dose rate from the MV beam with the dose rate from the kV beam. The factor $\alpha$ is influenced by the assumed MV dose rate, the assumed kV imaging frequency (frames per second), and the assumed kV image quality parameter (mAs/frame).

In one specific, non-limiting example, the dose optimization problem can be setup in MATLAB and optimized with the MOSEK toolbox (MOSEK ApS, Copenhagen, Denmark) for MATLAB, which uses dual-primal interior point methods. Optimizations can be performed on a PC with an Intel Core i7-2600 CPU, with 16 GB RAM. Optimization time varied depending on the number of constraints and the number of bixels. The simplest cases take on the order of a minute; although, some complicated cases required 90 minutes of computing time.

Figure 2:
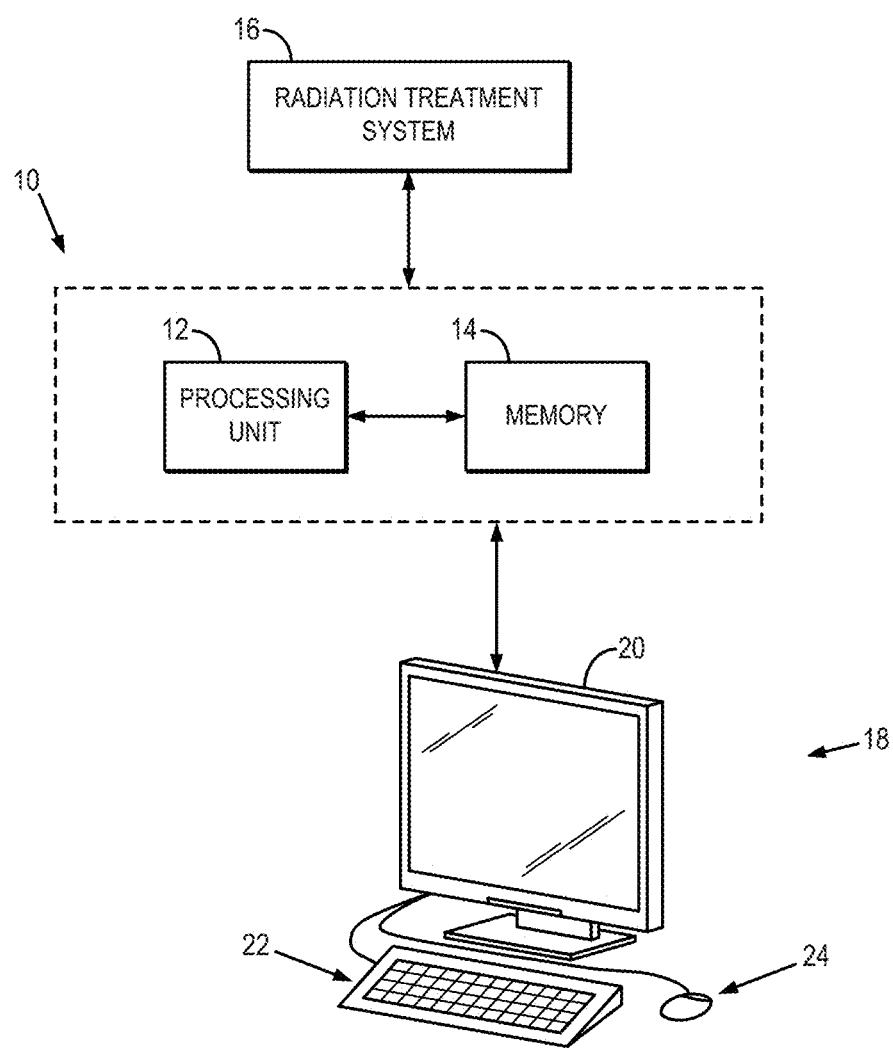
FIG. 2 is block diagram of an example radiation treatment planning system (TPS) that can implement some embodiments of the present invention.
Figures 3A, 3B, 3C, 3D:
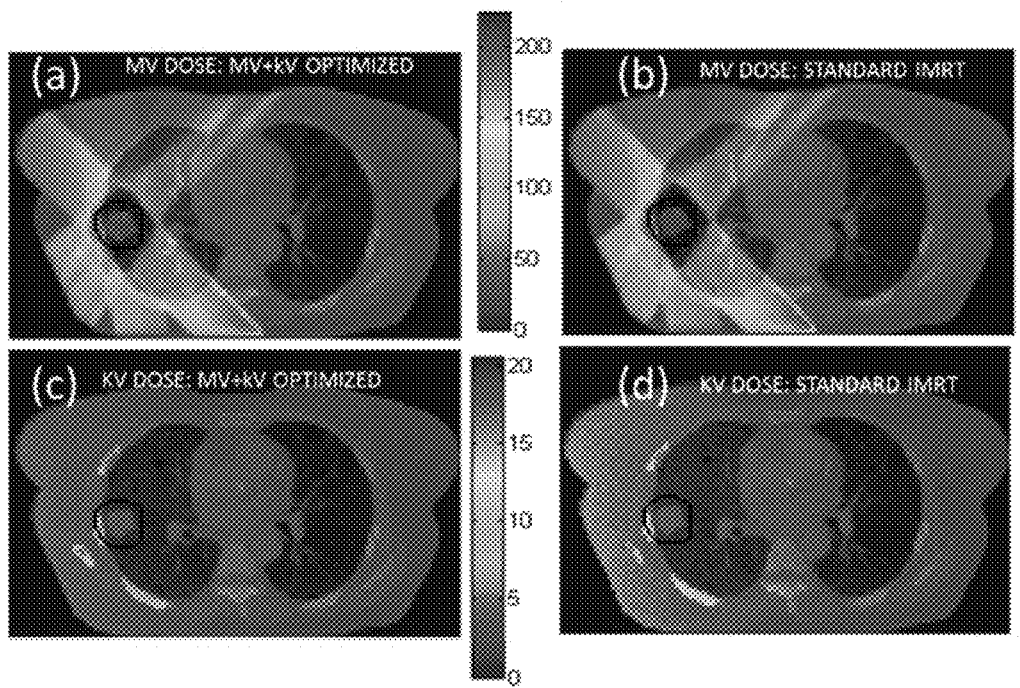
FIGS. 3A-3D illustrate MV and kV dose distributions for a lung patient using a large 20×27 $cm^2$ kV imaging aperture undergoing real-time intra-fractional tracking using either combined MV+kV optimization (FIGS. 3A and 3C) or conventional IMRT plus kV fluoroscopic imaging (FIGS. 3B and 3D). Dose is per fraction, based on 60 Gy prescription over 28 fractions.
Figures 4A, 4B, 4C, 4D:
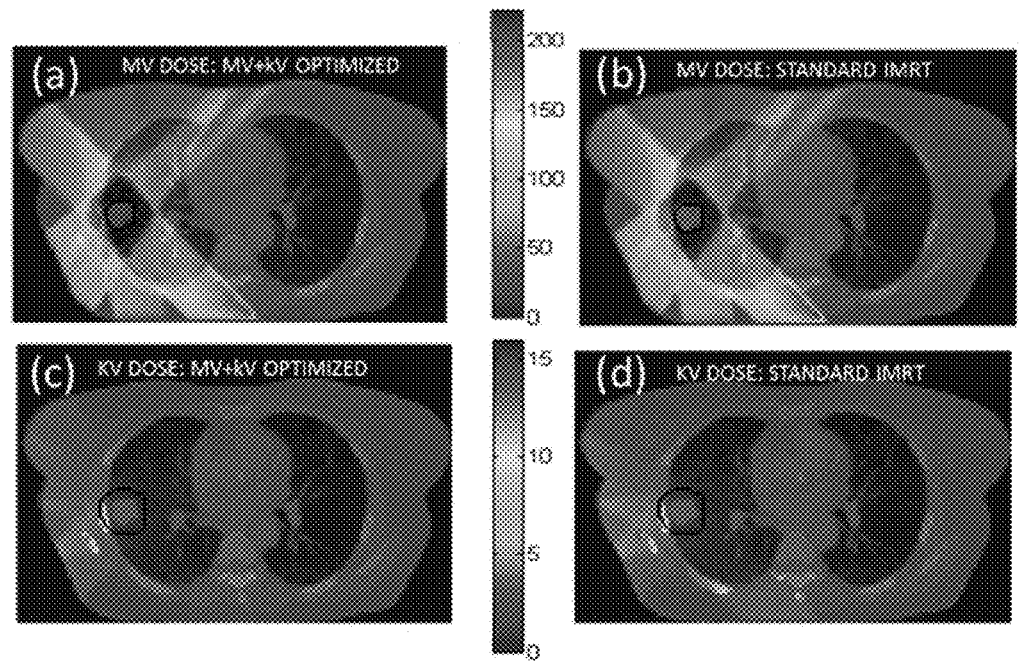
FIGS. 4A-4D illustrate MV and kV dose distributions for a lung patient using a small 5×5 $cm^2$ kV imaging aperture. Dose is per fraction, based on 60 Gy prescription over 28 fractions.
Figures 5A, 5B, 5C, 5D:
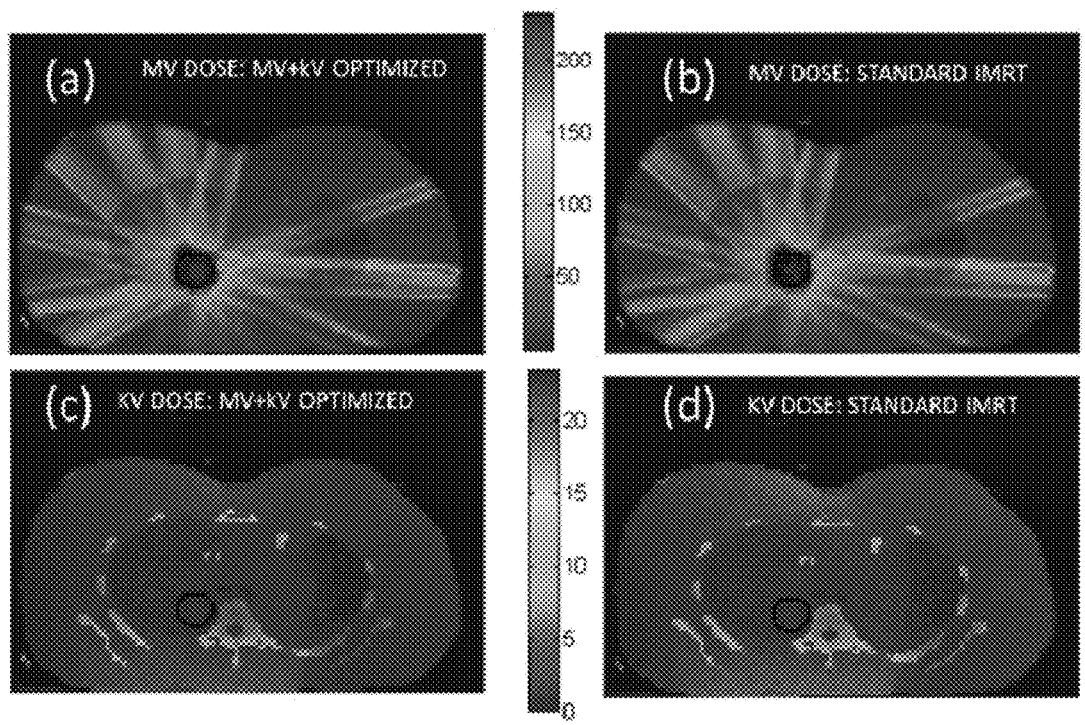
FIGS. 5A-5D illustrate MV and kV dose distributions for a second lung patient using a large 20×27 $cm^2$ kV imaging aperture undergoing real-time intra-fractional tracking using either combined MV+kV optimization (FIGS. 5A and 5C) or conventional IMRT plus kV fluoroscopic imaging (FIGS. 5B and 5D). Dose is per fraction, based on 60 Gy prescription over 28 fractions.
Figures 6A, 6B, 6C, 6D:
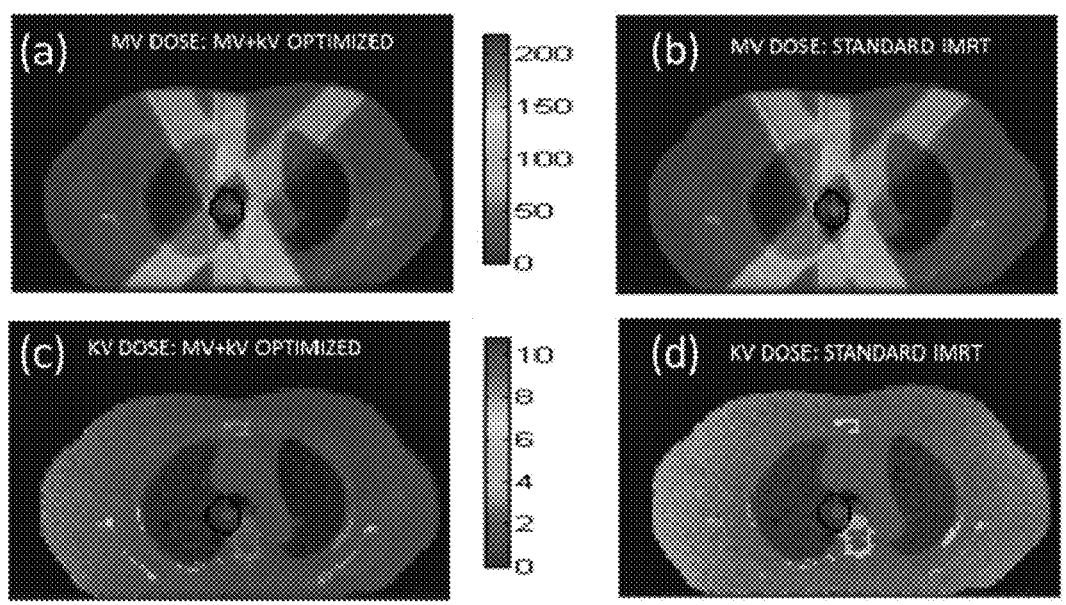
FIGS. 6A-6D illustrate MV and kV dose distributions for a third lung patient using a large 20×27 $cm^2$ kV imaging aperture undergoing real-time intra-fractional tracking using either combined MV+kV optimization (FIGS. 6A and 6C) or conventional IMRT plus kV fluoroscopic imaging (FIGS. 6B and 6D). Dose is cGy per fraction, based on 60 Gy prescription over 28 fractions.

The methods described above can be suitably implemented using a radiation treatment planning system. Referring now to FIG. 2, an example of such a radiation treatment planning system 10 is illustrated. The radiation treatment planning system 10 is preferably in communication with one or more radiation treatment systems 12, which may include any suitable image-guided radiation treatment system.

The radiation treatment planning system 10 generally includes a memory 14 that is operably coupled to a processor unit 16. As an example, the processor unit 16 can be a commercially available computer processor, such as those described above. The processor unit is configured to carry out one or more of the steps of the methods described above.

As an example, the memory 14 can include a plurality of memory elements, or can include a single memory element. In general, the memory 14 is configured to store information regarding patient data, a treatment target (e.g., a tumor located within a patient), imaging beam model data, treatment beam model data, dose matrices, and so on.

Preferably, the radiation treatment planning system 10 includes, or is otherwise in communication with, a user interface 18. As an example, the user interface 18 provides information to a user, such as a medical physicist. For example, the user interface 18 can include a display 20 and one or more input devices, such as a keyboard 22 and mouse 24.

EXAMPLE 1

Combined MV+kV Inverse Treatment Planning for Optimal kV Dose Incorporation in IGRT In this example, an investigation into the use of convex optimization tools to best integrate the kV imaging dose into the MV therapeutic dose was performed. As described above, the kV beam was treated as both an additional source of therapeutic radiation and as a method of imaging and dynamically tracking the tumor. This represents a radical departure from the existing paradigm where all current kV imaging dose is considered as unwanted and in excess of the planned MV treatment dose.

In this study, treatment plans were optimized for lung cancer patients using four different scenarios:
1. MV beam only optimization (standard IMRT) plus the addition of a fully open kV aperture (20 cm×27 cm).
2. MV beam only optimization (standard IMRT) plus the addition of a reduced kV aperture (5 cm×5 cm).
3. Combined MV+kV beam optimization with a fully open kV aperture (20 cm×27 cm).
4. Combined MV+kV beam optimization with a reduced kV aperture (5 cm×5 cm).

With these four different cases, it was possible to determine not only the imaging dose delivered to the patient, but also the effect on the overall treatment of considering the imaging dose at the point of planning. In order to verify that the treatment plan quality produced by the systems and methods of the present invention is comparable to that of a commercial system, a commercial treatment planning system was used to generate an IMRT plan for one of the 3D CRT patients used in this study, and compared the resultant DVH directly with a DVH for the same patient using MV beam only optimization and comparable constraints as used in the commercial system.

Results

FIGS. 3A-3D show the MV and kV dose distributions for patient #1 as tracked with an open kV aperture (20×27 cm$^2$), with and without the use of combined MV+kV optimization. While the MV dose distributions look similar between FIGS. 3A and 3B, the kV dose distributions are different. Across all voxels, lower kV doses are visible when using MV+kV optimization. This is a direct consequence of the MV+kV optimization engine treating the kV beam as a source of therapeutic radiation to both OARs and the PTV. When using MV+kV optimization (FIG. 3B) as opposed to conventional IMRT optimization with real-time kV tracking (FIG. 3D), skin dose from kV imaging is reduced from a maximum of 9.4 cGy in places to 5.9 cGy. The PTV receives 8.3 cGy per fraction from kV imaging beams when using MV+kV optimization, and 14.25 cGy per fraction when using regular IMRT with kV imaging.

FIGS. 4A-4D show similar plots as seen in FIGS. 3A-3D, acquired with the same experimental conditions, except now using a smaller (5×5 cm$^2$) imaging aperture. The difference in kV dose between the MV+kV optimization case, and the conventional IMRT with real-time tracking case, is not very noticeable. The smaller kV dose associated with a reduced aperture has less effect on the skin OAR dose constraints, and thus the introduction of kV dose into the treatment planning stage has relatively little effect.

FIGS. 5A-5D and FIGS. 6A-6D present similar data as FIGS. 3A-3D, but for a second and third patient. Once again, more kV dose is delivered when MV+kV optimization is not utilized. In patient #2 (FIGS. 5A-5D), the maximum skin dose is reduced from 10.2 cGy to 8.9 cGy, and in patient #3 (FIGS. 6A-6D), the maximum skin dose is reduced from 8.9 cGy to 5.2 cGy. PTV dose from kV beams varies from 3.36 cGy per fraction to 4.7 cGy per fraction.

Figure 7:
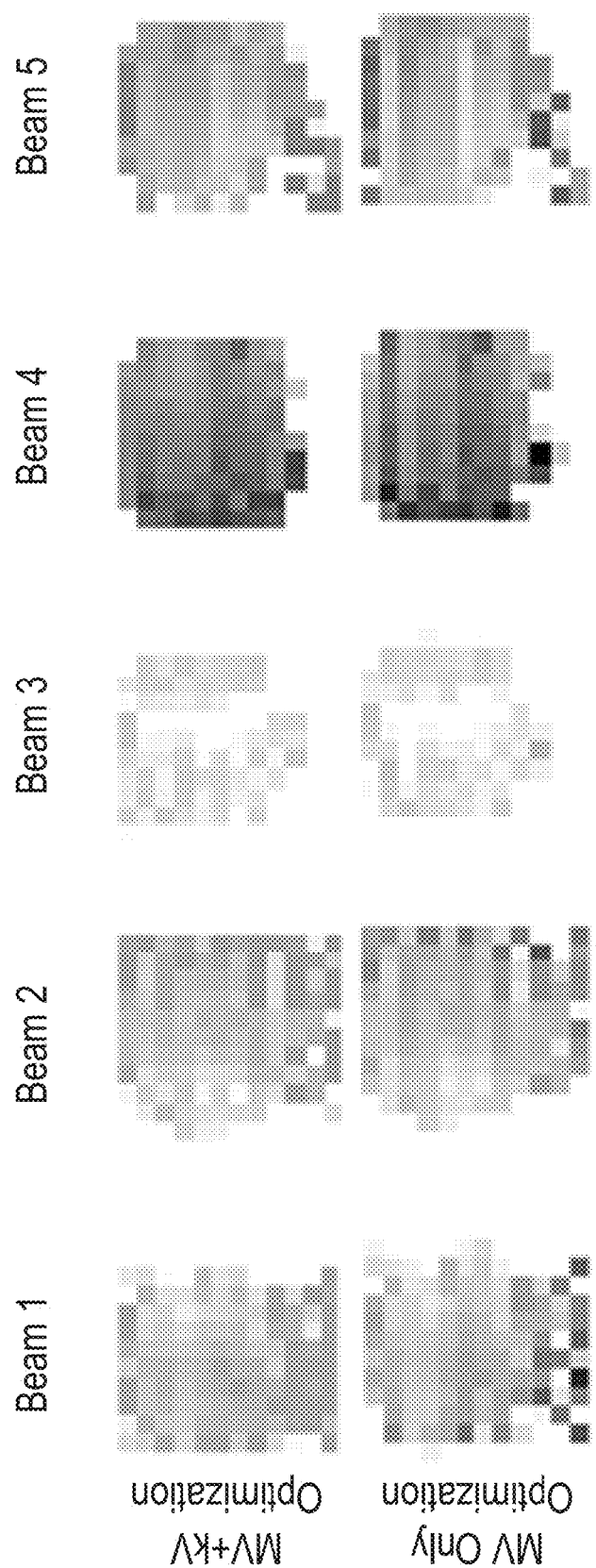
FIG. 7 illustrates beam's eye views (BEVs) for MV fluence, with and without MV+kV optimization, for the lung patient represented in FIGS. 3A-3D and assuming a 20×27 $cm^2$ imaging field. When combined MV+kV optimization is performed, fewer hot spots appear in the MV beams, spreading the dose across a larger number of bixels, resulting in a lower beam on time and lower kV imaging dose.

FIG. 7 shows the changes in beam's eye view ("BEV") of the dose for the first patient, across the MV+kV optimization case and the standard IMRT optimization case, with each beam scaled equivalently. Despite the fact that the MV dose distributions appear almost identical (as seen by the isodose lines in FIGS. 3A and 3C), the beam fluences used to reach the dose distributions are very different. The hot spots seen in the MV optimization only beam fluences will result in longer beam-on time, which in turn results in higher kV dose. Because the combined MV+kV optimization algorithm takes into account the skin dose from kV beams, high beam-on times may be indirectly punished by the planning algorithm, resulting in plans with fewer hot spots. This is reflected in the more evenly distributed MV bixel intensities seen with combined MV+kV dose optimization.

Figure 8:
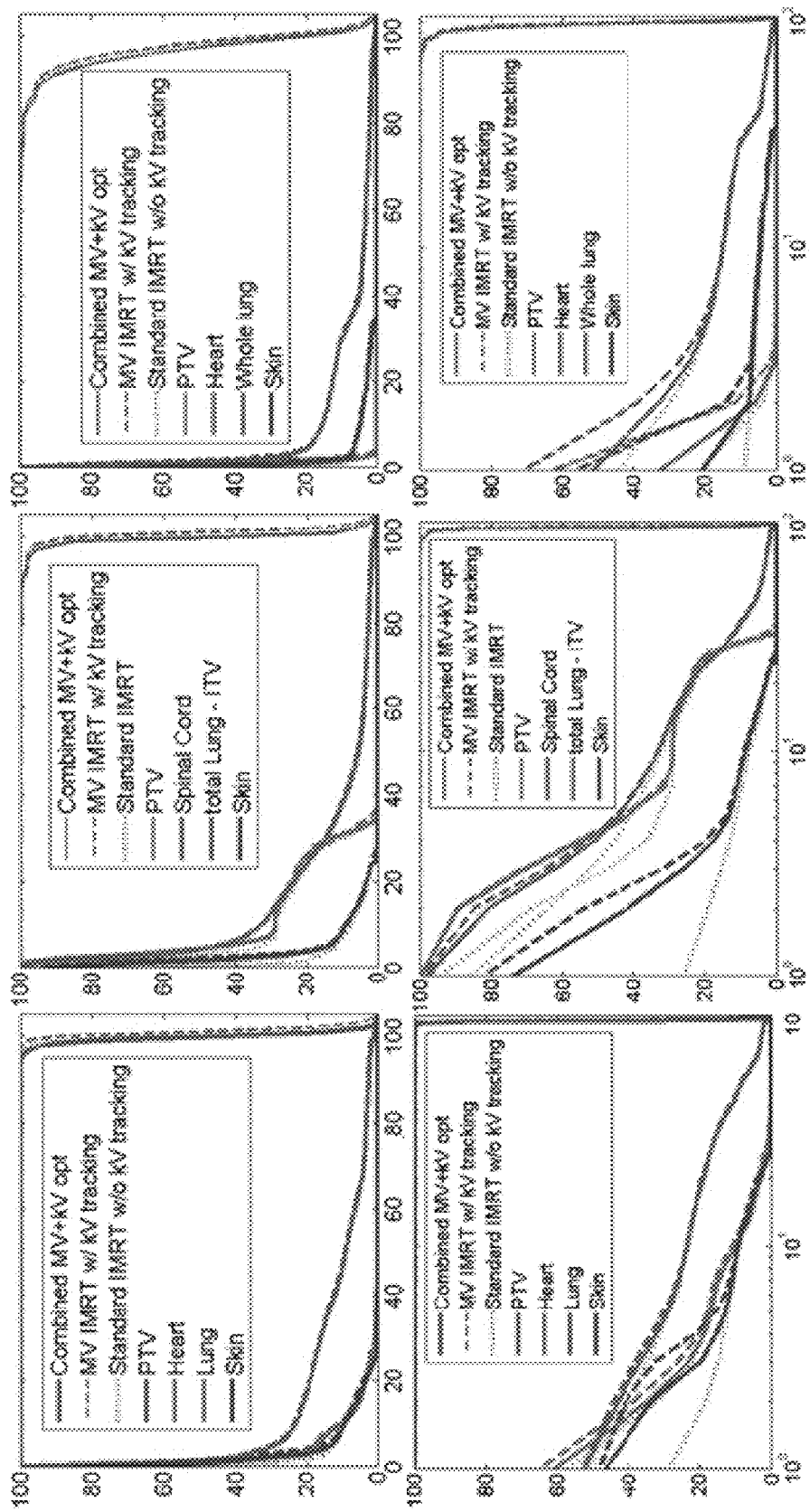
FIG. 8 illustrates lung dose volume histograms (DVHs) for three lung cancer patients with a 20×27 $cm^2$ kV imaging aperture. Percent dose (relative to 60 Gy prescription) on y-axis, percent volume on the x-axis. Top row displays linear scale, bottom row displays log scale on x-axis.

FIG. 8 shows DVH curves for three cases for both patients: (1) combined MV+kV optimization (solid line), (2) standard MV IMRT plus kV tracking (dashed line), and (3) standard MV IMRT with no kV imaging (dot line). Here case 3 is used as the reference standard. PTV coverage with MV+kV optimization more closely matches PTV coverage in the no-imaging case, and the OAR dose from MV+kV optimization approaches the OAR dose in the no-imaging case. Both OAR and PTV doses are higher in the MV IMRT with kV tracking case, and the difference in OAR dose is most striking for the skin, as the kV beam primarily deposits dose on the surface.

Figure 9:
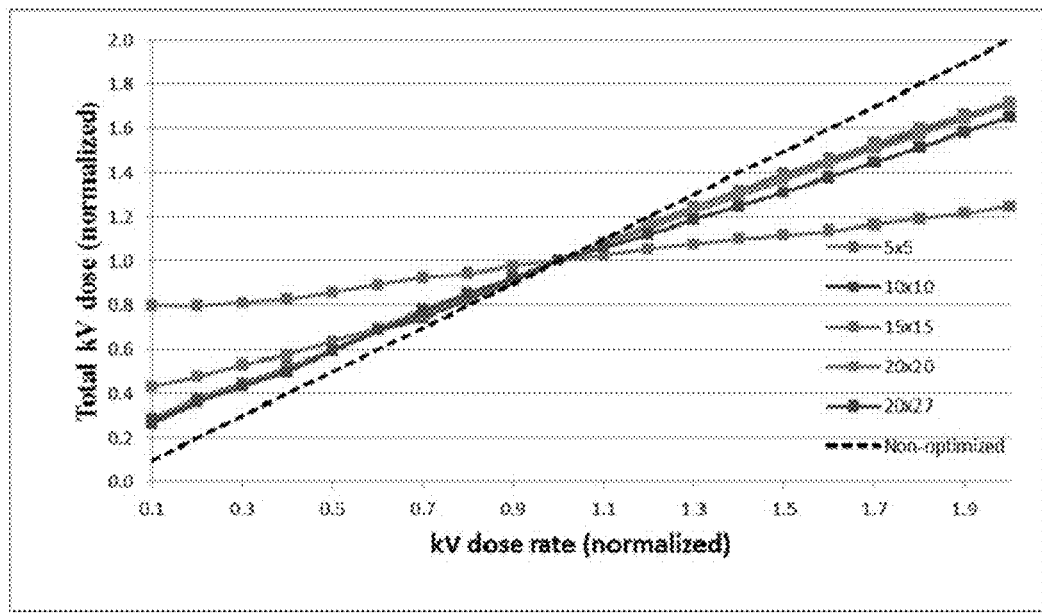
FIG. 9 illustrates total kV dose delivered (all volume) as a function of kV dose rate, for MV+kV optimization. kV imaging apertures from 5×5 $cm^2$ to 20×27 $cm^2$ are shown, and compared to a line for the relation between kV dose rate and total kV dose for non-optimized kV dose, for the lung patient represented in FIGS. 3A-3D.

FIG. 9 shows how the total kV dose delivered may vary as a function of the kV dose rate (mAs per frame×frame rate×duty cycle) for MV+kV optimization. Results are normalized to a frame rate of 15 fps. Because the mAs per frame, frame rate, duty cycle, and MV dose rate may change with different imaging requirements, this figure shows how the total kV dose varies as any of those parameters are changed. For example, when using a 5×5 cm$^2$ imaging aperture, reducing the frame-rate from 15 fps to 5 fps reduces the imaging dose rate to 33% of the reference dose rate, and consequently, from the figure, the total kV dose is reduced to approximately 81% of the reference total kV dose. When using a 20×27 cm$^2$ imaging aperture, an equivalent reduction in dose rate reduces the total kV dose to approximately 45% of the reference total kV dose. The curve for 10×10 imaging beam data is largely obscured by the curves for the larger sizes, because the curves for sizes larger than 5×5 cm$^2$ largely overlap.

Figure 10:
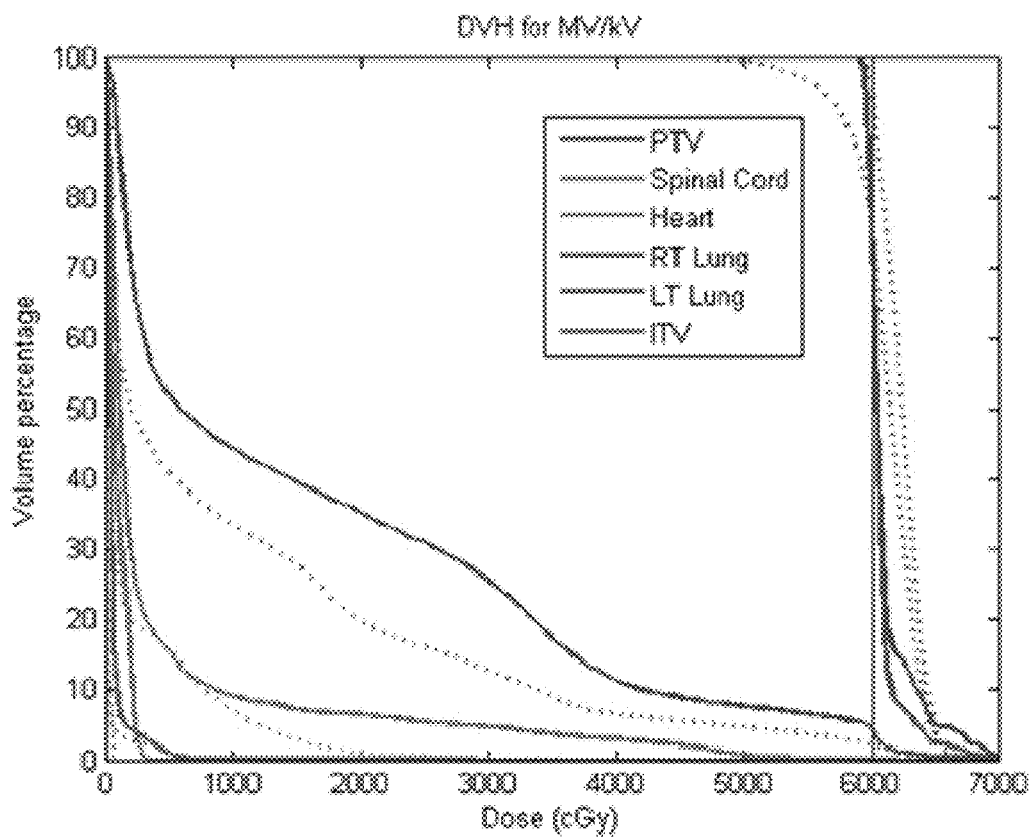
FIG. 10 illustrates DVH for the lung patient represented in FIGS. 3A-3D, using a TPS that implements the present invention (solid line) versus a commercial TPS that does not implement the present invention (dotted line), assuming a similar set of constraints modeled after clinically used constraints.

FIG. 10 compares the DVHs produced by an IMRT plan developed in the commercial treatment planning system for patient #1 (dashed lines), and the DVHs produced by our treatment planning system (solid lines), when incorporating similar constraints as used in the commercial system. In DVHs seen in FIG. 10, the dose to the PTV adheres more closely to the prescription when using the new TPS, however, OAR dose is sometimes lower when using the commercial system.

Discussion

As shown in FIGS. 3A-3D, the kV dose to the skin may be greatly reduced in the case of large aperture imaging when using MV+kV optimization as opposed to standard MV IMRT with unplanned real-time kV tracking. Here the skin dose was reduced from as high as 9.4 cGy per fraction to no more than 5.9 cGy per fraction, or a reduction of 37%. In addition, from the DVH curves presented in FIG. 8, it can be seen that excess PTV dose due to unplanned kV fluoroscopic radiation is now folded into the prescribed PTV dose, making the combined MV+kV optimization curve indistinguishable from the standard IMRT curve.

Relative to the 6 MV treatment beam, as shown in FIGS. 3A-3D, 4A-4D, 5A-5D, and 6A-6D, the kV skin dose from combined MV+kV is significantly lower. This is also shown by the skin DVH curves, where subtraction of the standard MV IMRT without kV tracking DVH curve from the kV tracking curves essentially removes most dose above 10% of prescription. However, from a diagnostic imaging point of view, the kV skin dose is still very high.

Here it should be noted that the high skin dose regions are localized (in that not all of the skin is receiving the optimized maxima of between 5 and 10 cGy), and that the chosen imaging parameters of 7.5 fps, with 80 mA and 32 ms per frame used in this particular study have been chosen to correspond to some imaging parameters reported elsewhere, but that these parameters can be readily changed to other values without departing from the teaching of the present invention. As an example, FIG. 8 illustrates that, for example, halving the frame rate to 3.75 fps lowers the kV dose for large apertures sizes by more than 50%.

The reduction in kV imaging dose from combined MV+kV optimization is essentially a result of two processes, both the lowering of the overall 6 MV beam on time, and the interplay between MV and kV skin dose constraints during optimization. In part, reduction in beam on time occurs because the kV imaging beam delivers dose to target, reducing the amount of MV monitor units required to treat the target. For example, in patient #1, where the PTV receives up to 14.25 cGy per fraction from the kV imaging beam prior to MV+kV optimization, the kV beam is delivering 6.65% of the prescription dose. When the kV beam is accounted for in the MV+kV optimization, the kV beam is only delivering 8.29 cGy per fraction, corresponding to 3.8% of the prescription. Therefore, the MV beam-on time is allowed to be reduced by about 3.8%. Similarly for patients #2 and #3, the contribution of kV imaging dose to the PTV may allow for beam on time reductions of 1.6% and 1%, respectively.

However, as seen in FIGS. 3A-3D, the skin dose reduction for patient #1 is much higher than 5%. Therefore, there is another factor involved in the lowering of beam on time. That factor is the additional burden of kV skin dose on the skin dose constraint in the optimization problem. Prior to the inclusion of kV dose, the skin dose constraint allows for MV beam weights with the maximally allowed skin dose. Adding kV imaging beams pushes the treatment plan past the constraints, therefore, the previously acceptable beam weights are now unacceptable. "Hot spots" in the MV beams are preferably removed, to lower both MV and kV dose to the skin and return the plan to one satisfying the skin dose constraints. This reduction is illustrated in FIG. 7, where the hot spots in the MV beams are lowered substantially when changing to MV+kV optimization. In changing from MV optimization to MV+kV optimization, the burden of delivering dose is forced to spread out across more bixels, reducing the beam on time for any one bixel.

Although, MOSEK optimization tools used in this study have been reported on favorably before for the task of radiotherapy optimization, it is still necessary to verify that plans produced using the combined MV+kV optimization engine are of suitable quality. Hence, a direct comparison of the DVHs produced by the MV+kV optimizer were made to the DVHs produced by an IMRT plan generated on a commercial TPS, for patient #1, using the same set of contours (FIG. 10). Due to the fact that it was not feasible to alter the commercial system to utilize kV dose and novel imaging constraints, only MV IMRT plans were compared. Although the DVHs are similar, there is some discrepancy between the plans produced by the commercial TPS and the research TPS, in some cases, may exceed the changes in DVH introduced by kV imaging in the research TPS. This is most likely a result of different optimizers used by the systems, and the fact that the combined MV+kV optimizer aims for a more conformal PTV dose at the expense of less optimal OAR doses than the commercial system.

As stated previously, this study assumed gated IMRT delivered to lung cancer patients, with kV imaging concurrent with the MV beam, in order to verify accurate patient positioning. Because the study was retrospective in nature, no specific imaging protocol is specified for tracking the patient motion when the treatment beam is off due to multi-leaf collimator ("MLC") segment steps or the target being outside the treatment gate window. In certain embodiments, an external surface tracking through either IR markers or 3D surface imaging can be used during beam off situations, and kV motion tracking can be used to track lung tumor motion and verify positioning during radiation delivery. This scenario corresponds directly to the combined MV+kV dose results presented in this work.

Alternatively, the parameterization of the MV+kV dose optimization algorithm may be modified in order to provide for kV tracking both within and without the gating window. There are two basic approaches to accomplish this. In the first approach, static treatment on a gated target is still assumed, but with kV tracking occupying a greater part of the duty cycle than the treatment beam delivery. In order to accomplish this, the dose optimization algorithm will assign a weighting factor to the kV dose calculation to account for the discrepancy in duty cycles. For example, if the gating window occupies 20% of the respiratory cycle, a weighting factor of 5 will be assigned, so that every second of MV beam on time corresponds to 5 seconds of kV beam on time. This technique may be further refined for more sophisticated cases, such as imaging at a lower frame rate while the treatment beam is off than when the treatment beam is on, in order to lower the imaging dose while maintaining kV tracking during non-treated phases of breathing. This is explored in FIG. 9, where the relationship between the relative kV dose rate and total kV dose delivered has been calculated.

For a given kVp and aperture size, the kV dose rate is a function of the mAs per frame, the frame rate, and the duty cycle. From the perspective of the treatment planning algorithm, increasing the kV duty cycle to five times the MV duty cycle is indistinguishable from increasing the kV dose rate by a factor of five, thus, FIG. 8 can show (for a limited range of increases in dose rate) how such duty cycle manipulations allow this technique to be used for imaging during the entire respiratory phase, even with gated delivery.

Because of the increase in imaging dose with constant imaging outside the gated window, the presented method may be preferred for 4D IGRT techniques that do not require the use of gating, but instead deliver conformal radiation through the respiratory cycle by dynamically tracking the tumor using the MLC, the radiation source, or the patient treatment couch. As real-time 3D positional knowledge of the target is preferred for 4D IGRT methods as an input parameter, the direct target tracking provided by real-time MV+kV optimization is an ideal match.

For real-time kV intra-fractional tracking of lung tumors, incorporation of the kV imaging into the MV treatment dose through the use of combined MV+kV inverse optimization has the potential to substantially lower the kV skin dose when compared to standard IMRT with kV tracking, without lowering the overall quality of the treatment plan in terms of PTV coverage and dose fall off on surrounding normal tissues. The benefits of combined MV+kV optimization were found to be preferred for situations that previously resulted in high kV dose, such as large apertures and high mAs or framerate settings. This technique allows for direct quantification of the kV imaging dose before the start of treatment delivery, and for the formation of treatment plans that are optimal in terms of both MV therapeutic and kV imaging dose delivered.

EXAMPLE 2

Combined MV+CBCT Inverse Treatment Planning for Optimal Dose Incorporation in IGRT Cone beam CT ("CBCT") is increasingly used in patient setup for IMRT. Daily CBCT may provide effective localization, however, it introduces concern over excessive imaging dose. Previous studies investigated the calculation of excess CBCT dose, however, no study has yet treated this dose as a source of therapeutic radiation, optimized in consideration of PTV and OAR constraints. Here is presented a novel combined MV+kV inverse optimization engine to weave the CBCT and MV dose together such that CBCT dose is used for both imaging and therapeutic purposes. This may mitigate some of the excess imaging dose effects of daily CBCT and, more importantly, allow complete evaluation of the CBCT dose prior to treatment.

The techniques described here can be applied, in certain embodiments, to the case of daily CBCT. In contrast to real time fluoroscopy, in which typically five or seven gantry angles will be chosen for treatment, with CBCT, images are acquired at full 360 degree geometry, decreasing the likelihood of kV hot spots on the skin. Second, whereas with real time fluoroscopy, the kV imaging beam on time for each gantry angle is dynamically linked to the corresponding MV beam on time, with CBCT, the beam on time across all projections is static, regardless of MV beam activity. Finally, the imaging parameters required to quality imaging (mAs) are different between CBCT and fluroscopy.

In this example, the EGSnrc Monte Carlo system was used to model a Varian Trilogy CBCT system and 6 MV treatment beam. Using the model, the dose to patient from treatment beam and imaging beam was calculated for ten patients. The standard IMRT objective function was modified to include CBCT dose. Treatment plan optimization using the MOSEK optimization tool was performed retrospectively with and without assuming kV radiation dose from CBCT, assuming one CBCT per fraction. Across ten patients, the CBCT delivered peaks of between 0.4% and 3.0% of the prescription dose to the PTV, with average CBCT dose to the PTV between 0.3% and 0.8%. By including CBCT dose to skin as a constraint during optimization, peak skin dose is reduced by between 1.9% and 7.4%, and average skin dose is reduced by 0.2% to 3.3%. Pre-treatment CBCT may deliver a substantial amount of radiation dose to the target volume. By considering CBCT dose to skin at the point of treatment planning, it is possible to reduce patient skin dose from current clinical levels, and to provide patient treatment with the improved accuracy that daily CBCT provides.

It will be apparent to one of skill in the art that other dose calculation methods can be used. Examples include, but are not limited to, Acros models, convolution-superposition models, and pencil-beam models.

The IMRT optimization problem may be formalized as the minimization of a quadratic problem, $$\min_{x \in \mathbb{R}^n} |Dx - p|^2; \qquad (5)$$

in which x is an n×1 matrix of beam weights for each bixel used for treatment or imaging, p is an m×1 matrix of prescription dose, specifying the prescription to each of n voxels in the treatment volume, and D is an m×n influence matrix specifying the dose from each bixel to each voxel. This quadratic objective function is subject to a number of constraints, $$x \geq 0 \text{ and } Hx - q > 0 \qquad (6).$$

The first constraint, x≥0, ensures that all beamlets are restricted to non-negative values, and the second constraint equation, Hx−q>0, encompasses all upper/lower bound dose constraints and imaging constraints. In conventional treatment plan optimization, the term q specifies upper and lower bounds allowed to specific voxels, with the matrix H playing a similar role as the matrix D in the objective function, specifying the dose contribution from each bixel to each voxel in the set of constrained voxels. In the case of combined MV+kV optimization, however, an imaging constraint is also required, such that H may be written as, $$H = \begin{bmatrix} H_{DOSE} \\ H_{IM} \end{bmatrix}. \qquad (7)$$

In this case, $H_{DOSE}$ corresponds to the traditional dose constraint used in IMRT optimization, with each row of $H_{DOSE}$ corresponding to a voxel in the patient. The dot product of a row of $H_{DOSE}$ with the vector x gives the total dose to the voxel. The voxels used in $H_{DOSE}$ come from both the PTV and the OARs. In this study, and the skin was automatically contoured and used as an OAR. Additionally, the structures contoured in the clinically used 3DCRT plans were exported from a commercial treatment planning system (Pinnacle, Philips, Netherlands) and imported into the research TPS using tools provided by the Computation Environment for Radiotherapy Research (CERR). The skin OAR was automatically segmented. The PTV and other OARs were taken from the previous commercial treatment plan.

In general, $H_{IM}$ may be used to define constraints on the imaging beams, specifying minimum and maximum beam on times for imaging beams, without directly considering dose. In order to perform dual MV+CBCT dose optimization, the new constraint $H_{IM}$ was introduced to specify the requirement of CBCT imaging, and is a generalized case of the first constraint equation applied only to the CBCT bixels. The effect of the matrix elements of $H_{IM}$ is to set upper and lower bounds on the CBCT bixels, $$x_{CBCT} \geq \alpha, \ x_{CBCT} \leq \alpha \qquad (8);$$

where $\alpha$ is a weighting factor balancing the dose rate from the MV beam with the dose rate used during CBCT. In this embodiment it is required that the CBCT delivers dose exactly equal to frequency and image acquisition parameters (including mAs per frame, the number of projections used in actual CBCT acquisition, and the number of projections used for dose calculation) specified in the treatment protocol; in this study, an imaging frequency of once per fraction was assumed. The problem was setup in MATLAB (Mathworks, Natick, Mass.) and optimized with the MOSEK toolbox (MOSEK ApS, Copenhagen, Denmark) for MATLAB, which uses dual-primal interior point methods. Optimizations were performed on a PC with an Intel Core i7-2600 CPU, with 16 GB RAM. Optimization time varied depending on the number of constraints and the number of bixels. The simplest cases take on the order of a minute, though some complicated cases required 90 minutes of computing time.

Three scenarios were compared: MV beam only optimization (standard IMRT) with no CBCT imaging; MV beam only optimization (standard IMRT) plus retrospective CBCT, and combined MV+CBCT beam optimization.

Patient Modeling

The treatment plans from ten previously treated lung cancer patients were used in this study. CT phantom (RMI 465, Gammex, Middleton, Wis.) was imaged in the CT planning simulator in order to provide data for the ramp function used in the Monte Carlo dose calculations for CBCT dose. The media used for the ramp function included air, lung tissue, adipose, water, muscle, inner bone, and cortical bone. The program "ctcreate," distributed with EGSnrc system, was used to convert the ten patient CT scans to the appropriate file format (".egsphant" files) for MC simulation in the EGSnrc system. For MV beam MC simulation, a simpler ramp function comprised only of air, lung, water, and bone was used because MV dose delivery is dominated by the Compton interaction, which is dependent on Z/A.

Beam Modeling

BEAMnrc was used to model both 6 MV treatment beams and 125 kV CBCT beams. In each case, beam models were developed from the schematics of the Varian Trilogy and Varian Trilogy on-board-imager (OBI) systems. 144 MV beam elements (bixels), each 5×5 mm², were modeled and superimposed to map a 6×6 cm² aperture at isocenter. Each MV bixel phase space file was generated from 500M histories. Only one kV phase space file was required, for an asymmetrical beam opening of 19.8×26.5 cm passing through a half-bowtie filter.

Dose Calculation

For each patient, gantry angles were chosen corresponding to the clinical implemented treatment plan, and MV bixel computations were performed for each bixel location, for each gantry angle. Similarly, kV dose calculations were performed with the CBCT phase space file at 180 locations, each separated by two degrees, to simulate CBCT geometry. Because in practice, CBCT are acquired from 660 projections, the output from each projection is scaled appropriately. The MV dose calculations used 3M histories each, and the kV dose calculations used 16M histories each. Dose calculations were performed on a combination of a distributed computing cluster, and a PC with an Intel Core i7-2600 CPU, with 16 GB RAM. One of skill in the art will recognize that the calculations can be optimized for a variety of parallel or nonparallel systems.

Normalized output from DOSXYZnrc were calibrated to machine settings. For the 6 MV beams, a machine calibration 0.85 cGy/MU at 10 cm depth in water for the MV beam was used, with a 400 MU/min dose rate. For CBCT dose, the model assumed 20 mA/20 ms per frame, with 660 frames captured.

Results

Figures 11A, 11B:
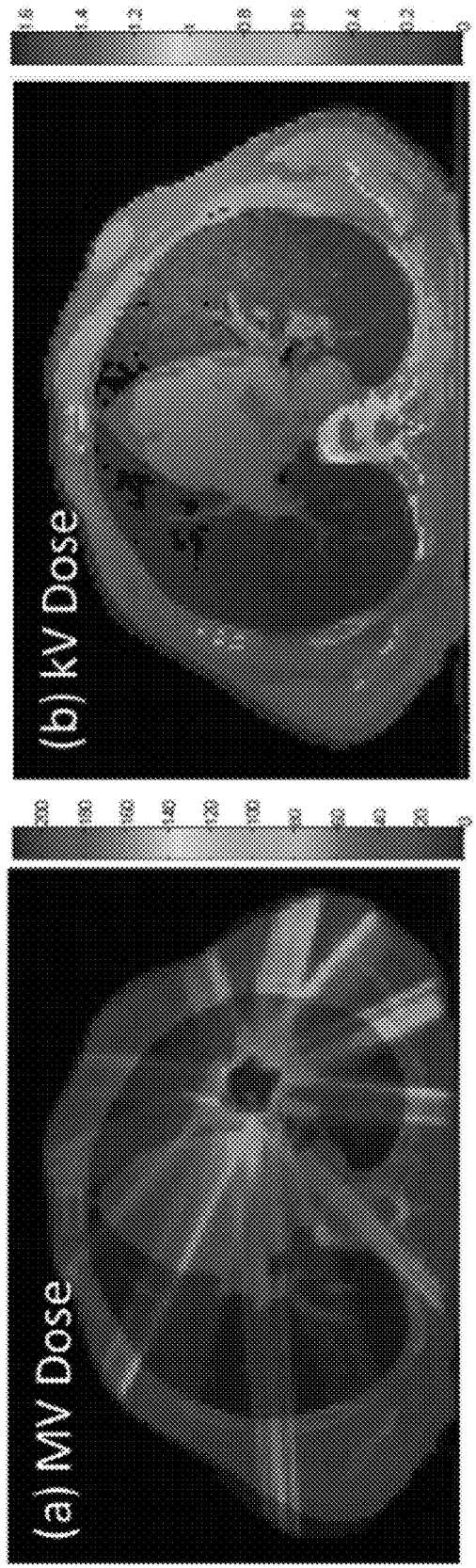
FIGS. 11A-11B show MV and kV cone beam computed tomography (CBCT) dose distributions when using MV+CBCT dose optimization for an example lung patient. CBCT dose is completely static, whether using MV+CBCT optimization or conventional MV only optimization with retrospective CBCT. The MV dose distribution differs slightly between the two cases, in a way described quantitatively in Table 1.

FIGS. 11A-11B show MV and kV CBCT dose distributions when using MV+CBCT dose optimization for one of the ten patients in the dataset. CBCT dose was completely static, whether using MV+CBCT optimization or conventional MV only optimization with retrospective CBCT. The total dose distribution differed slightly between the two cases, as quantitatively described in Table 1 below. Differences in the distributions were difficult to visually observe between MV and MV+CBCT treatment plans. FIG. 11A shows the MV dose distribution (dose is per fraction, based on a prescription of 70 Gy over 35 fractions, and FIG. 11B shows the CBCT dose distribution.

TABLE 1

| | Skin (cGy) | | | PTV (cGy) | | Skin Dose Reduction (%) | |
|---|---|---|---|---|---|---|---|
| | Max | Mean | Mean | Max | Mean | | |
| Patient | CT | CT | Total | CT | CT | Max | Mean |
| 1 | 1.21 | 0.30 | 5.31 | 3.07 | 0.65 | 2.04 | 0.73 |
| 2 | 1.57 | 0.25 | 4.49 | 0.43 | 0.35 | 0.86 | −1.24 |
| 3 | 0.95 | 0.36 | 3.59 | 1.13 | 0.50 | 1.60 | 0.47 |
| 4 | 1.09 | 0.35 | 8.40 | 3.08 | 0.57 | 1.99 | 0.66 |
| 5 | 1.09 | 0.25 | 3.96 | 0.91 | 0.76 | 1.88 | 1.21 |
| 6 | 2.70 | 0.32 | 5.16 | 3.81 | 0.90 | 4.47 | 0.74 |
| 7 | 1.34 | 0.39 | 7.75 | 1.04 | 0.84 | 2.50 | 1.78 |
| 8 | 1.14 | 0.42 | 10.51 | 0.84 | 0.61 | 2.09 | 0.60 |
| 9 | 0.83 | 0.34 | 3.82 | 0.64 | 0.53 | 1.29 | 0.32 |
| 10 | 0.57 | 0.32 | 6.65 | 0.43 | 0.34 | 1.04 | 0.27 |

Table 1 shows a summary of results for CBCT+MV optimization across 10 patients. All numbers are in cGy for a single fraction, based on 200 cGy/fraction prescription, unless otherwise noted. In general, CBCT dose to skin is a small fraction of total dose to skin; however, locally, CBCT may deliver high dose to skin, which exerts pressure on the treatment plan to lower skin dose from the MV beams. CBCT+MV optimization results in reductions in total average skin dose between 0.27% and 1.78%.

Figure 12:
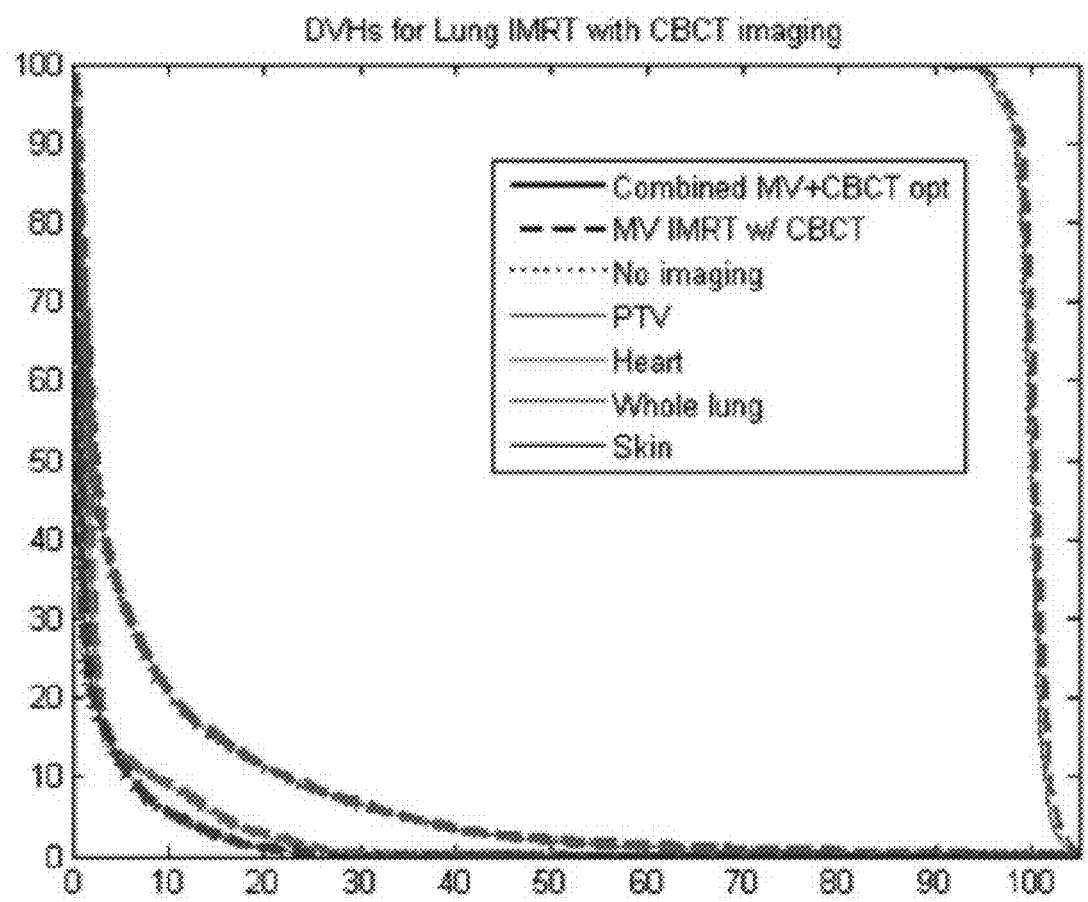
FIG. 12 shows a set of DVH curves corresponding to the treatment plan shown in FIG. 11, in all three cases: no CBCT imaging dose (base case), unplanned for CBCT imaging dose, and optimized with CBCT imaging dose.

FIG. 12 shows a set of DVH curves corresponding to the treatment plan shown in FIGS. 11A and 11B, in all three cases: no CBCT imaging dose (base case, dotted lines), unplanned for CBCT imaging dose (dashed lines), and optimized with CBCT imaging dose (solid lines). DVH for the target is slightly overdosed for standard MV IMRT with CBCT. Combined MV+CBCT optimization more closely approaches the no-imaging case than the non-optimized daily CBCT case.

Figure 13:
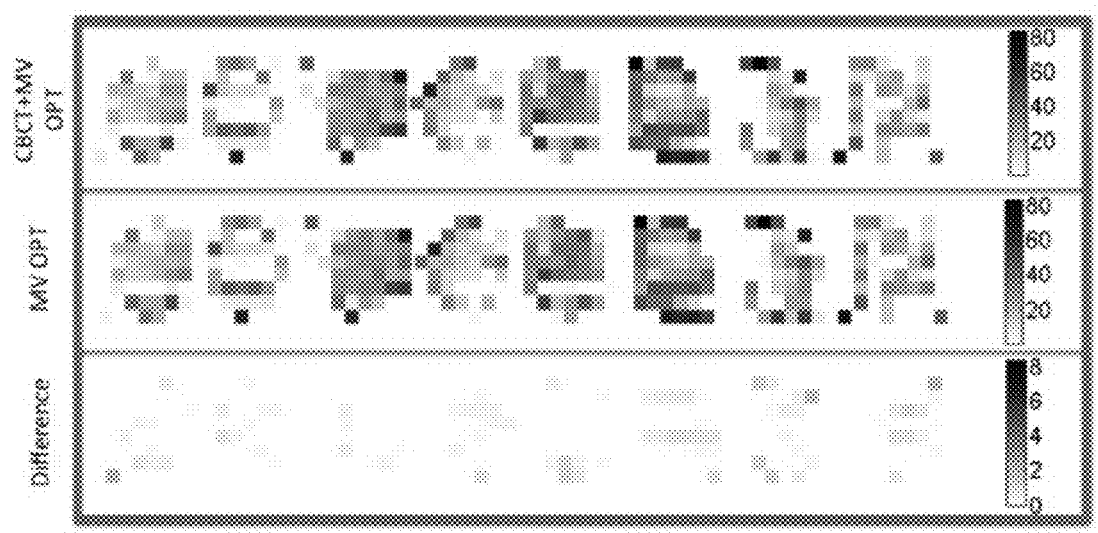
FIG. 13 shows changes in MV beam fluences for one of the treatment plans with the incorporation of MV+CBCT treatment planning. Just as the differences in MV dose distributions between the MV and MV+CBCT optimized cases would be difficult to detect unassisted visually, the difference between the fluence maps is also subtle.

The three DVH curves for each structure appear extremely similar; however, slight overdosing is visible to the PTV in the non-optimized CBCT case. FIG. 13 shows changes in MV beam fluences for one of the treatment plans with the incorporation of MV+CBCT treatment planning. Just as the differences in MV dose distributions between the MV and MV+CBCT optimized cases would be difficult to detect unassisted visually, the difference between the fluence maps is also subtle.

As shown in the summary of Table 1, CBCT tends to deliver peak doses to the PTV between 0.3% and 3%, with averages PTV coverage typically less than 1% of prescription. However, the integration of CBCT dose may allow for lower skin dose, by forcing the MV beam fluences to change in order to compensate for CBCT skin dose. This change is shown in FIG. 13.

Incorporating CBCT dose into the treatment plan allows for improvements to treatment plan quality, and perhaps more importantly, it allows physicians and medical physicists to prescribe motion management strategies such as CBCT with the confidence of knowing the dosimetric effect ahead of time. However, the results presented comparing dose with CBCT to the no-imaging case make the conservative assumption that the imaging is being performed for verification only, and that the same treatment margins are used for the imaging and non-imaging cases. In practice, it will likely be the case that daily CBCT will allow for smaller treatment margins than in the no-imaging case, and in fact, it is likely that the quantification of the margin reduction will depend both on the imaging modality chosen (e.g., CBCT vs real-time fluoroscopy) as well as the imaging parameters and resultant image quality.

EXAMPLE 3

Combined MV+kV Imaging with Direct Aperture Optimization

As described above, combined MV+kV optimization can be implemented for real-time fluoroscopy, CBCT guided therapy, and other radiation therapy techniques that use x-ray imaging for guidance. The optimization methods described above implement ideal fluence based optimization, in which a set of ideal beam weights for a particular treatment are calculated without any consideration to the ease of delivery given the constraints of MLC motion.

Traditionally, dose optimization is followed by an MLC leaf sequencing step, at which point the dose calculation is repeated on the actual, deliverable plan in order to verify plan quality. This traditional method has the advantage that, because of the relative ease of optimization, it can be modeled as a convex problem and therefore can guarantee that any local minimum is a global minimum. This classical approach to IMRT optimization is increasingly becoming replaced, however, with direct aperture optimization ("DAO"). In general, DAO techniques attempt to incorporate information on MLC leaf positions into the treatment planning algorithm in order to avoid a leaf sequencing step.

As will now be described, the MV+kV optimizations described above can be modified to implement DAO techniques.

Direct aperture optimization is especially appropriate for MV+kV fluoroscopy optimization. In DAO, the beam-on times are optimized for each aperture at each gantry angle, rather than optimizing bixel fluence, which is merely a proxy for beam-on time. Therefore, with DAO, the kV imaging dose required to perform real-time imaging can be more accurately predicted at the time of treatment planning. DAO is also known to reduce the monitor unit ("MU") used in delivery, which can further reduce the kV dose from MV+kV delivery.

To demonstrate the applicability of MV+kV optimization using DAO, some of the experiments described above were repeated for a single patient using DAO.

Materials and Methods

Aperture Dose Calculation. A method for producing a dose influence matrix using Monte Carlo calculations is described above. In the dose influence matrix, D, each row corresponds to a beam element, or bixel, and each column corresponds to a point, or voxel, in the patient. In the case of DAO, each row of a matrix $D_{ap}$ corresponds to an entire aperture, rather than to a single bixel. On the one hand, this difference may provide a computational advantage because it may dramatically reduce the dimensionality of the problem. However, this difference may also introduce complications into the mathematical formulation. Specifically, the new formulation means that each row of the dose influence matrix, $D_{ap}$, is not linearly-independent because the rows are now the sum of sometimes overlapping bixels. Also, as the MLC leaf positions are moved in the optimization, the rows of D must change; in other words, the matrix $D_{ap}$ is not static. This in particular changes the optimization strategies described above.

In order to minimize the time spent recalculating values for the matrix, $D_{ap}$, at each iteration, rather than re-calculating the values, fast set operations can be performed to quickly add and subtract values from the matrix. The update equation for rows of $D_{ap}$ may be written, $$D_{ap}(i,:)=D_{ap}(i,:)-D(S_{ini}\backslash S_{new},:)+D(S_{new}\backslash S^{ini},:) \qquad (9);$$

where $S_{ini}$ is the set of bixels initially in the aperture, $S_{new}$ is the set of bixels in the new aperture, and "\" denotes the following set operation:

$$B\backslash A \equiv \{x \in B | x \notin A\} \qquad (10).$$

Figures 14A, 14B:
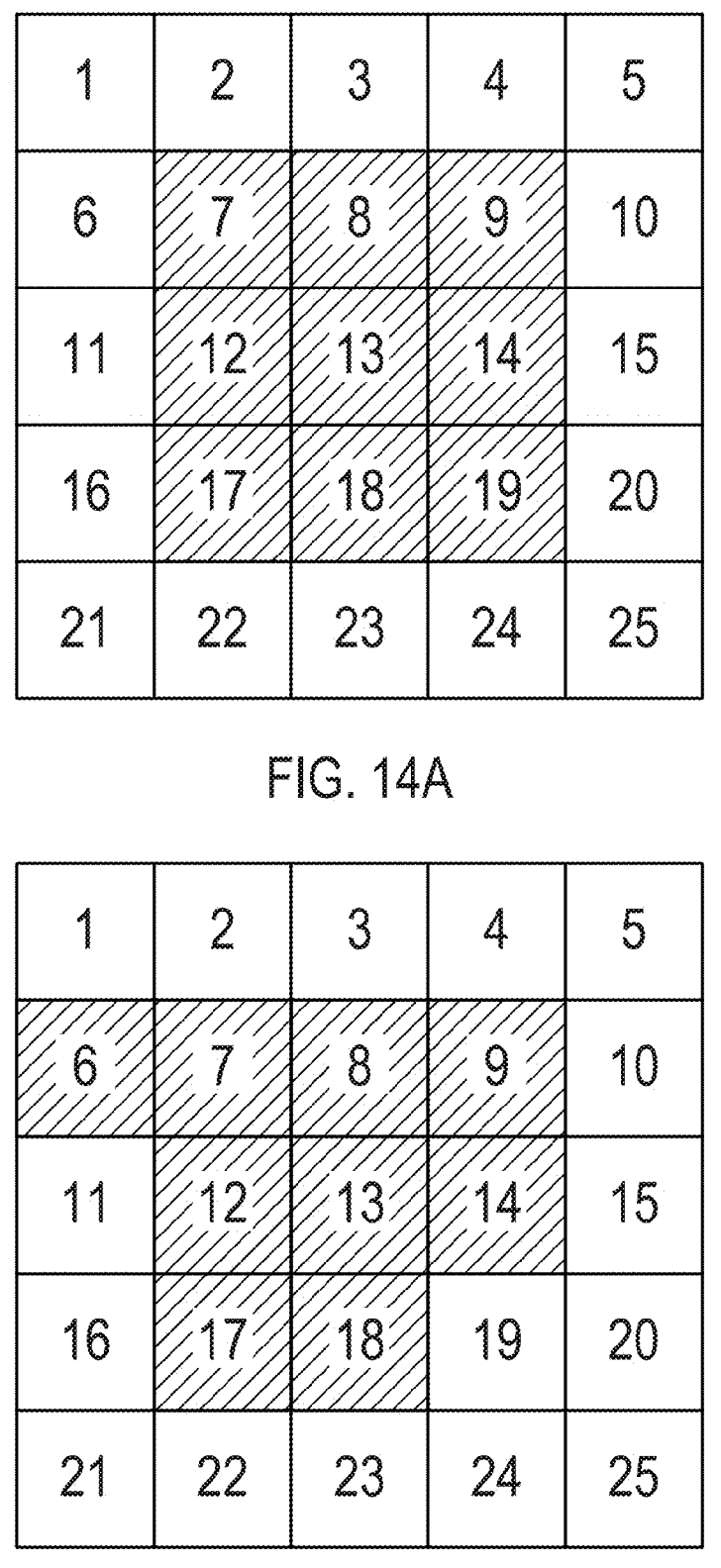

For example, the $i^{th}$ aperture in the matrix $D_{ap}$ may be a square aperture centered in an array of 5×5 pixels, and may therefore initially be composed of pixels in the set $S_{ini}=\{7, 8,9,12,13,14,17,18,19\}$, as shown in FIG. 14A. At an iteration in the optimization process, the algorithm may direct the top-left MLC to open by one space, and at another step, the algorithm may direct the bottom-right MLC to close by one space. This new aperture may be described by the set $S_{new}=\{6, 7,8,9,12,13,14,17,18\}$, as shown in FIG. 14B. Therefore, the update function for the matrix $D_{ap}$ may be written as, $$D_{ap}(i,:)=D_{ap}(i,:)-D(19,:)+D(6,:) \qquad (11).$$

A BEV technique can be used to find acceptable limits on the MLC leaf positions to envelop the target. The contour of the tumor is back-projected to the MLC plane for each gantry angle, and a set of MLC leaf positions to encompass the tumor is calculated.

Optimization Algorithm. For direct aperture optimization, the algorithm optimizes both aperture shapes (e.g., by changing the rows of the matrix $D_{ap}$) and the aperture weights. A combination of simulated annealing and interior-point methods can be used for the optimization because, while the selection of MLC leaf positions is not a convex problem, the optimization of beam weights, once leaf positions are fixed, is a convex problem and can therefore be efficiently solved with deterministic algorithms.

To initialize the optimization problem, the BEV apertures are used as a starting point and an interior-point method is used to find the optimal beam weights. Then, the order of the MLC leaves is randomized, and shifts in leaf positions are optimized using simulated annealing. As one example, simulated annealing can be implemented by randomly calculating the shift for each leaf position from a Gaussian density function with width, $$\sigma = 1 + (A-1)e^{-\log(n_{succ}+1)/T_0^{step}} \quad (12);$$

Parameterized by the initial width, A, and the cooling parameter, $T_0^{step}$, as a function of the number of successful iterations, $n_{succ}$. Success is defined as either a change that results in an improved cost, or a change that does not result in an improved cost, but is allowed to proceed with some probability, $$P = 2B \cdot \frac{1}{1 + e^{\log(n_{succ}+1)/T_0^{prob}}}; \quad (13)$$

parameterized by the initial probability, B, and the cooling parameter, $T_0^{prob}$, also as a function of the number of successes. Any suggested shift in MLC leaf position is immediately rejected, and a new shift calculated, if the proposed shift results in a leaf position that violates the constraints (e.g., a leaf opening wider than allowed by the constraint on maximal leaf position, or closing to overlap with the position of its paired leaf on the opposite side). In principle, a large number of physical constraints on MLC leaf positions are possible to implement, such as minimal/maximal distances between paired leaves, and maximal distances for leaves to move between apertures.

MLC leaf positions are optimized using the simulated annealing algorithm described above. However, beam weights for each aperture are optimized using a different method, such as the interior-point method of MOSEK. The frequency with which beam weights are updated, compared to the frequency of MLC position updates, is a parameter that may be tuned to affect optimization performance. For example, the beam weights can be updated after updating all of the MLC leaf positions, or at some regularly spaced interval of MLC updates, or randomly according to some probability distribution. As one specific example, the beam weights can be updated after every twenty MLC position updates.

Results

Figure 15:
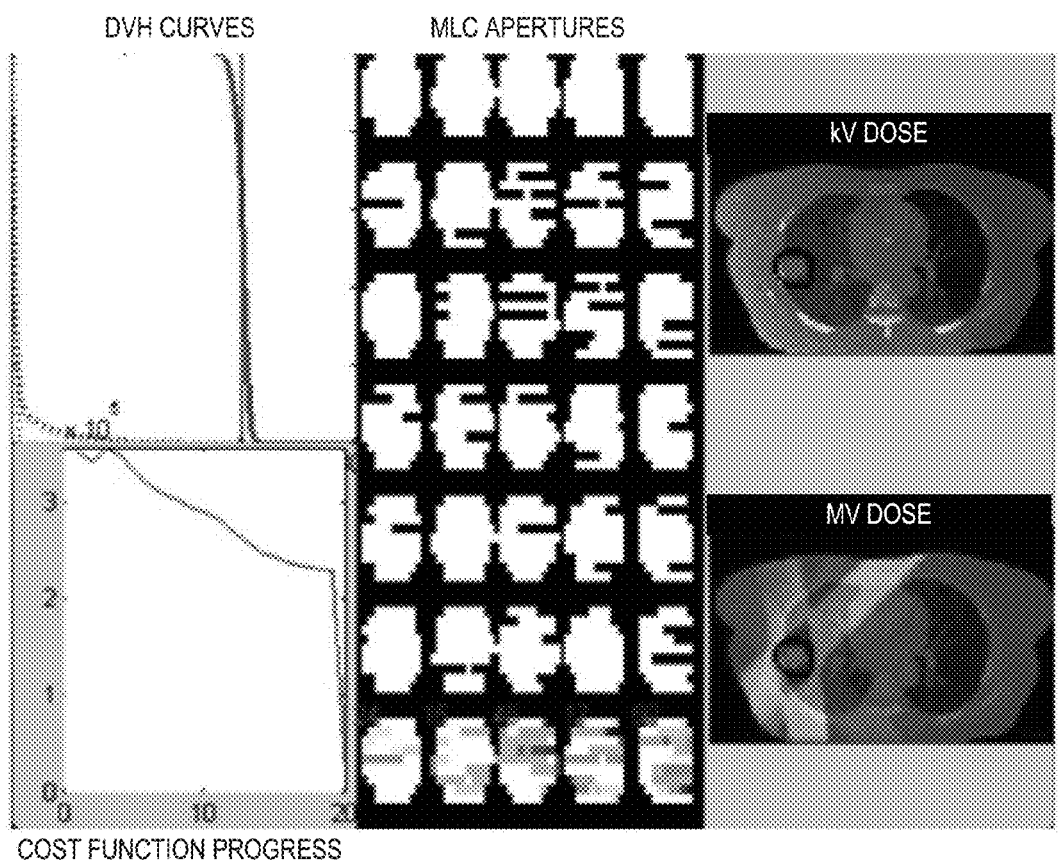
FIG. 15 illustrates a graphical user interface displaying a performance of an MV+kV optimization algorithm that incorporates direct aperture optimization.

FIG. 15 shows a snapshot of the direct aperture optimization program running for one of the previously treated patients. In the top left, the current DVH at the point the snapshot was taken is displayed, and in the bottom left, the progress of the cost function is plotted. The middle section shows the beam aperture shapes. Each column corresponds to a different gantry angle, the first row shows the maximum opening (determined by BEV), the last row shows the superposition of the various apertures for the given angle, with the total number of MU indicated, and the middle rows show each of the aperture shapes for each gantry angle. The top right and bottom right display a dose map for the kV and MV contributions to the total dose, respectively. The real-time display allows the user to cancel the optimization and change parameters if the plan appears to be evolving in a way that will not satisfy the independent human judgment of the dosimetrist.

Figures 16A, 16B, 16C:
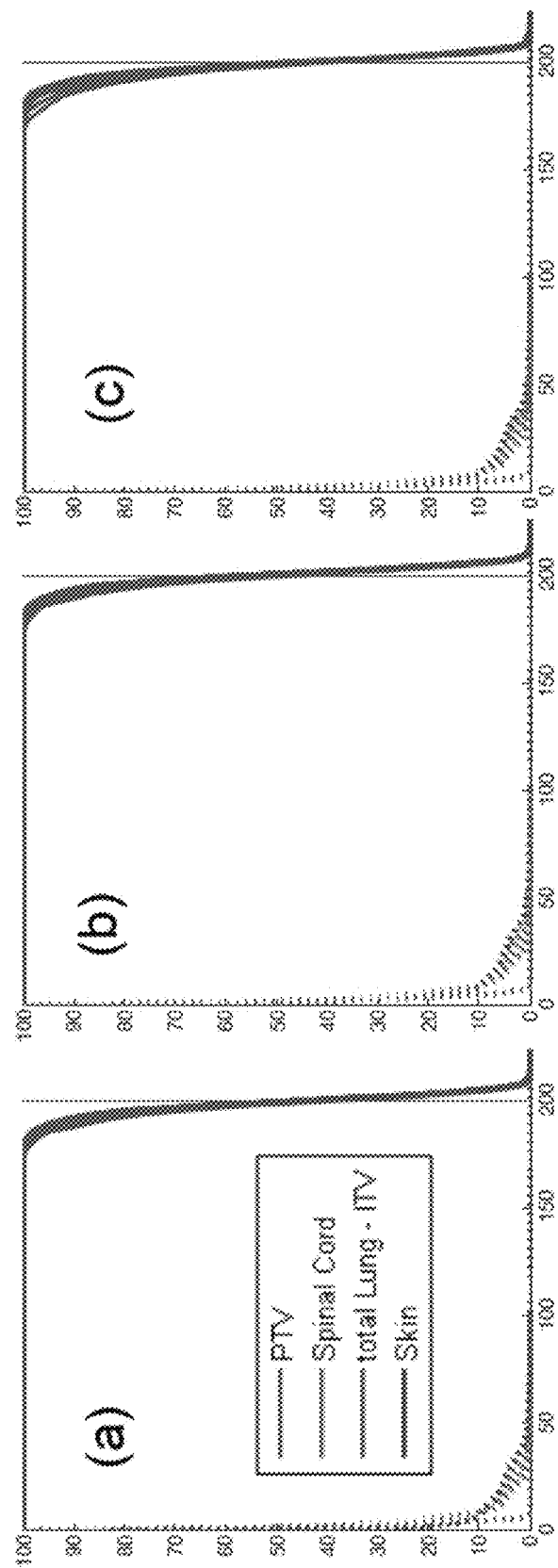
FIGS. 16A-16C show DVH curves associated with twenty independent repetitions of an optimization task.

FIG. 16A-16C show DVH curves associated with the twenty independent repetitions of the optimization task. FIG. 16A shows the DVH curves for MV only optimization without kV imaging, FIG. 16B shows the DVH curves for MV optimization with non-optimized kV imaging, and FIG. 16C shows the DVH curves for MV+kV optimization.

Figure 17:
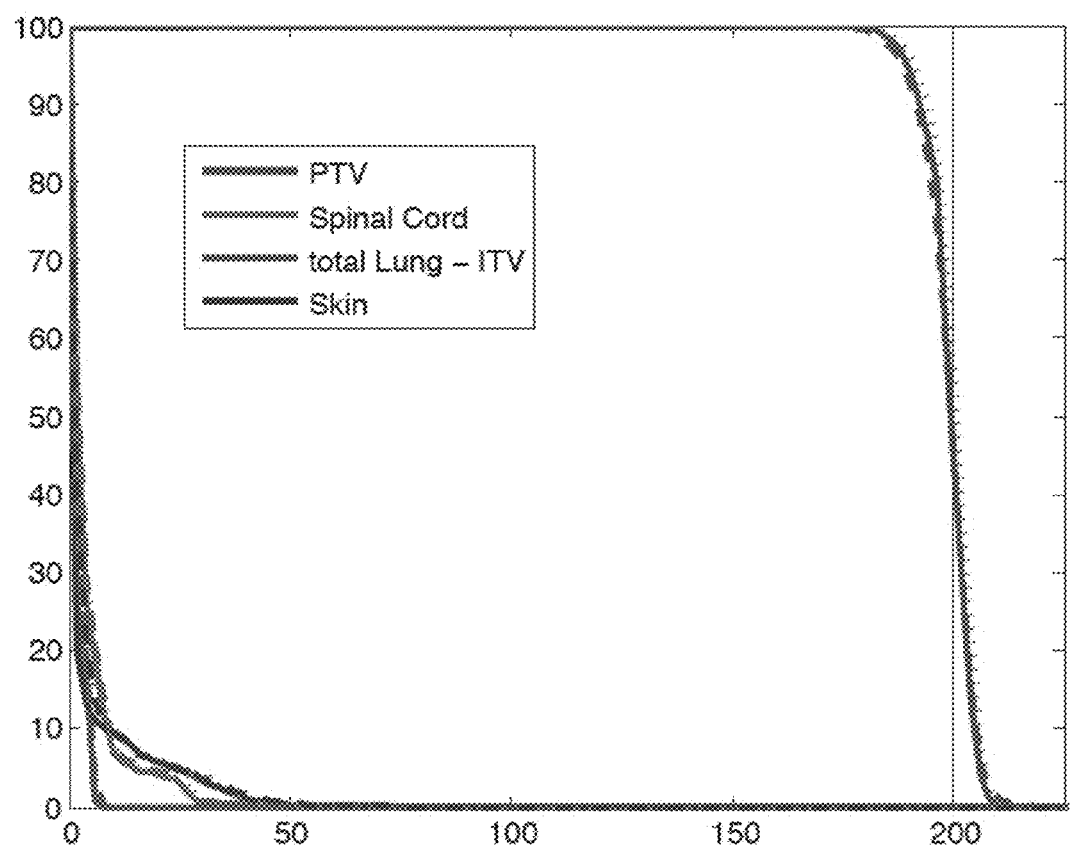
FIG. 17 shows DVH curves averaged across twenty optimizations for no imaging (solid), non-optimized imaging (dotted), and MV+kV optimized imaging (dashed).

FIG. 17 compares the DVH curves associated with the average performance for the three methods. The average performance DVH curve is that curve associated with an average of the dose distributions across the twenty trials. Across twenty optimizations, combined MV+kV IMRT resulted in an average of 4.56% reduction in peak skin dose, an average reduction of 2.74% reduction in mean skin dose, an average of 4.92% reduction in peak skin dose reduction from kV beams, and an average 5.98% reduction in mean skin dose from kV beams. Both non-optimized and MV+kV optimized imaging beams delivered, on average, mean dose of approximately 1 cGy per fraction to the target, with peak doses to target of approximately 6 cGy per fraction.

When using DAO, MV+kV optimization is shown to result in improvements to plan quality in terms of skin dose, when compared to the case of MV optimization with non-optimized kV imaging. The combination of DAO and MV+kV optimization may improve upon the method of direct fluence based MV+kV optimization to further allow for real-time imaging without excessive dose.

The present invention has been described in terms of one or more preferred embodiments, and it should be appreciated that many equivalents, alternatives, variations, and modifications, aside from those expressly stated, are possible and within the scope of the invention.

The invention claimed is:

1. A computer-implemented method for producing a radiation treatment plan for a radiation treatment system that includes an imaging radiation source that emits an imaging radiation beam and a treatment radiation source that emits a treatment radiation beam, the steps of the method comprising:
   (a) providing patient data to a treatment planning system;
   (b) providing a dose calculation model of the imaging radiation beam to the treatment planning system;
   (c) providing a dose calculation model of the treatment radiation beam to the treatment planning system;
   (d) directing the treatment planning system to produce a radiation treatment plan by optimizing an objective function based on the first and second dose calculation models, subject to a constraint that accounts for beam-on time for both the imaging radiation beam and the treatment radiation beam.

2. The method as recited in claim 1, wherein the constraint in step (d) encompasses upper and lower bounds of imaging dose constraints and treatment dose constraints.

3. The method as recited in claim 1, wherein the constraint in step (d) accounts for the beam-on time for the imaging radiation beam using a matrix in which each row of the matrix specifies the beam-on time for the imaging radiation beam orthogonal to a given beamlet of the treatment radiation beam.

4. The method as recited in claim 3, wherein each row of the matrix includes a weighting factor that balances a dose rate from the treatment radiation beam with a dose rate from the imaging radiation beam.

5. The method as recited in claim 1, wherein the dose calculation model of the imaging radiation beam models the imaging radiation source as a kV x-ray source.

6. The method as recited in claim 5, wherein the dose calculation model of the imaging radiation beam models the imaging radiation source as a kV x-ray source in a fluoroscopy imaging system.

7. The method as recited in claim 5, wherein the dose calculation model of the imaging radiation beam models the imaging radiation source as a kV x-ray source in a cone beam computed tomography (CBCT) imaging system.

8. The method as recited in claim 1, wherein the dose calculation model of the treatment radiation beam models the treatment radiation source as an MV x-ray source.

9. The method as recited in claim 8, wherein the dose calculation model of the treatment radiation beam models the treatment radiation source as an MV x-ray source in an intensity-modulated radiation therapy (IMRT) system.

10. The method as recited in claim 8, wherein the dose calculation model of the treatment radiation beam models the treatment radiation source as an MV x-ray source in a volumetric modulated arc therapy (VMAT) system.

11. The method as recited in claim 1, wherein the imaging radiation source and the treatment radiation source are different radiation sources.

12. The method as recited in claim 1, wherein the objective function minimized in step (d) includes a dose influence matrix based on the first and second dose calculation models.

13. The method as recited in claim 12, wherein the objective function minimized in step (d) includes a dose influence matrix in which each row of the dose influence matrix represents an aperture of a multi-leaf collimator and each column of the dose influence matrix represents a point in a patient.

14. The method as recited in claim 13, wherein the dose influence matrix is updated while minimizing the optimization function to account for moving leaf positions in the multi-leaf collimator.

15. The method as recited in claim 1, wherein step (b) includes providing the dose calculation model of the imaging radiation beam to the treatment planning system by retrieving the dose calculation model of the imaging radiation beam from at least one of a data storage or memory external to the treatment planning system.

16. The method as recited in claim 1, wherein step (b) includes providing the dose calculation model of the imaging radiation beam to the treatment planning system by retrieving the dose calculation model of the imaging radiation beam from at least one of a data storage or memory internal to the treatment planning system.

17. The method as recited in claim 1, wherein step (b) includes providing the dose calculation model of the imaging radiation beam to the treatment planning system by generating the dose calculation model of the imaging radiation beam using the treatment planning system.

18. The method as recited in claim 1, further comprising displaying the radiation treatment plan on a graphical user interface.

19. The method as recited in claim 18, wherein displaying the radiation treatment plan on the graphical user interface comprises displaying at least one of a dose from the imaging radiation beam, a dose from the treatment radiation beam, and a dose from a combination of both the imaging radiation beam and treatment radiation beam.

* * * * *

UNITED STATES PATENT AND TRADEMARK OFFICE
CERTIFICATE OF CORRECTION

PATENT NO. : 9,782,607 B2
APPLICATION NO. : 14/818808
DATED : October 10, 2017
INVENTOR(S) : Rodney Wiersma et al.

It is certified that error appears in the above-identified patent and that said Letters Patent is hereby corrected as shown below:

In the Specification

Column 18, Line 44, Eq. (9):
"$D_{ap}(i,:) = D_{ap}(i,:) - D(S_{ini} \setminus S_{new},:) + D(S_{new} \setminus S^{ini},:)$"
Should be:
--$D_{ap}(i,:) = D_{ap}(i,:) - D(S_{ini} \setminus S_{new},:) + D(S_{new} \setminus S_{ini},:)$--.

Signed and Sealed this
Fourteenth Day of November, 2017

Joseph Matal
*Performing the Functions and Duties of the*
*Under Secretary of Commerce for Intellectual Property and*
*Director of the United States Patent and Trademark Office*